United States Patent
Takeuchi et al.

(10) Patent No.: US 12,055,538 B2
(45) Date of Patent: Aug. 6, 2024

(54) FUSIONS AND METHOD FOR DETECTING SAME

(71) Applicant: JAPANESE FOUNDATION FOR CANCER RESEARCH, Tokyo (JP)

(72) Inventors: Kengo Takeuchi, Tokyo (JP); Seiji Sakata, Tokyo (JP); Yuki Togashi, Tokyo (JP); Naoya Fujita, Tokyo (JP); Ryohei Katayama, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 627 days.

(21) Appl. No.: 17/144,776

(22) Filed: Jan. 8, 2021

(65) Prior Publication Data

US 2021/0140943 A1 May 13, 2021

Related U.S. Application Data

(62) Division of application No. 16/070,110, filed as application No. PCT/JP2017/001118 on Jan. 13, 2017, now Pat. No. 10,921,311.

(30) Foreign Application Priority Data

Jan. 15, 2016 (JP) ................................ 2016-006471

(51) Int. Cl.
| | | |
|---|---|---|
| C07H 21/04 | (2006.01) | |
| A61K 31/519 | (2006.01) | |
| A61K 38/00 | (2006.01) | |
| A61P 35/00 | (2006.01) | |
| C07K 14/82 | (2006.01) | |
| C12N 9/12 | (2006.01) | |
| C12N 9/88 | (2006.01) | |
| C12N 15/113 | (2010.01) | |
| C12N 15/62 | (2006.01) | |
| G01N 33/50 | (2006.01) | |
| G01N 33/574 | (2006.01) | |
| C12Q 1/6853 | (2018.01) | |
| C12Q 1/686 | (2018.01) | |
| C12Q 1/6886 | (2018.01) | |

(52) U.S. Cl.
CPC ........ *G01N 33/5011* (2013.01); *A61K 31/519* (2013.01); *A61K 38/005* (2013.01); *A61P 35/00* (2018.01); *C07K 14/82* (2013.01); *C12N 9/12* (2013.01); *C12N 9/88* (2013.01); *C12N 15/113* (2013.01); *C12N 15/62* (2013.01); *C12Y 207/11025* (2013.01); *C12Y 402/01047* (2013.01); *G01N 33/57446* (2013.01); *C12Q 1/6853* (2013.01); *C12Q 1/686* (2013.01); *C12Q 1/6886* (2013.01)

(58) Field of Classification Search
None
See application file for complete search history.

(56) References Cited

U.S. PATENT DOCUMENTS

| | | | |
|---|---|---|---|
| 2009/0029357 A1* | 1/2009 | Inazawa | ............... C12Q 1/6886 435/6.12 |
| 2010/0075320 A1 | 3/2010 | Salgia | |
| 2011/0230545 A1 | 9/2011 | Mano et al. | |
| 2013/0102006 A1 | 4/2013 | Takeuchi et al. | |
| 2015/0299810 A1 | 10/2015 | Kassis | |
| 2016/0010068 A1 | 1/2016 | Bastian et al. | |

FOREIGN PATENT DOCUMENTS

| | | |
|---|---|---|
| JP | 4303303 | 7/2009 |
| JP | 2012-100628 | 5/2012 |
| WO | 2011/162295 | 8/2013 |
| WO | 2014/130975 | 8/2014 |

OTHER PUBLICATIONS

International Search Report dated Apr. 4, 2017, 6 pages.
International Preliminary Report on Patentability dated Jul. 17, 2018, includes Written Opinion, 16 pages.
Salgia R., et al., Molecular Cloning of Human Paxillin, a Focal Adhesion Protein Phosphorylated by P210BCR/ABL., J. Biol. Chem., 1995, vol. 270, No. 10, p. 5039-5047, p. 5040, right column, 3rd paragraph, 9 pages.
Bisht K.K., et al., "GDP-mannose 4, 6-dehydratase is a Cytosolic Partner of Tankyrase 1 that Inhibits its poly (ADP-ribose) Polymerase Activity", Mol. Cell. Biol., 2012, vol. 32, No. 15, p. 3044-3053, p. 3045, left column, 3rd to 4th paragraphs, 10 pages.
Zheng Z., et al., "Anchored Multiplex PCR for Targeted Next-Generation Sequencing", Nat. Med. 2014, vol. 20, No. 12, p. 1479-1484, Abstract, 6 pages.
Palanisamy N., et al., "Rearrangements of the RAF Kinase Pathway in Prostate Cancer, Gastric Cancer and Melanoma", Nat. Med., 2010, vol. 16, No. 7, p. 793-798, Abstract, Figure 1 p. 797, left column, 4th paragraph, 8 pages.
Kieran, M.W., "Targeting BRAF in Pediatric Brain Tumors", Am. Soc. Clin. Oncol. Educ. Book, 2014, p. e-436-440, Abstract, 5 pages.
Ciampi, R., et al., "Oncogenic AKAP9-BRAF Fusion is a Novel Mechanism of MAPK Pathway Activation in Thyroid Cancer", J. Clin. Invest., 2005, vol. 115, No. 1, p. 94-101, Abstract, 9 pages.

(Continued)

*Primary Examiner* — Celine X Qian
(74) *Attorney, Agent, or Firm* — Rankin, Hill & Clark LLP

(57) ABSTRACT

It is intended to reveal a polynucleotide serving as a novel causative gene of a cancer and, on the basis of this finding, to provide a method for detecting the polynucleotide or a polypeptide encoded thereby, a kit and a primer set for the detection, a method for screening for a substance that inhibits the polypeptide, and a pharmaceutical composition for the treatment of a cancer, containing the inhibiting substance. The detection method of the present invention detects a BRAF fusion protein or a fusion gene encoding the fusion protein, or a PXN or GMDS fusion protein or a fusion gene encoding the fusion protein in a digestive organ-derived sample obtained from a subject.

2 Claims, 3 Drawing Sheets

Specification includes a Sequence Listing.

(56) References Cited

OTHER PUBLICATIONS

Lugo, T.G., et al., "Tyrosine Kinase Activity and Transformation Potency of bcr-abl Oncogene Products", Science, 1990, vol. 247 (4946), p. 1079-1082, 4 pages.

Stephens, et al., "95-Kilodalton B-Raf Serine/Threonine Kinase: Identification of the Protein and its Major Autophosphorylation Site", Molecular and Cellular Biology, Sep. 1992, vol. 12, No. 9, p. 3733-3742, 10 pages.

McMahon, "RAF Translocations Expand Cancer Targets", Nature Medicine, vol. 16, No. 7, Jul. 2010, p. 749-750, 2 pages.

Needleman, et al., "A General Method Applicable to the Search for Similarities in the Amino Acid Sequence of Two Proteins"., J. Mol. Biol., 1970, 48 (3), p. 443-453, 6 pages.

Metzker, "Sequencing Technologies—the Next Generation", Nature Reviews/Genetics, vol. 11, Jan. 2010, p. 31-46, 16 pages.

Heid, et al., "Real Time Quantitative PCR", Genome Research, 1996, 6 (1), p. 986-994, 10 pages.

Takeuchi, et al., "KIF5B-ALK, A Novel Fusion Oncokinase Identified by an Immunohistochemistry-based Diagnostic System for ALK-positive Lung Cancer", Clin. Cancer Res. 2009; 15 (9), May 1, 2009, p. 3143-3149, 8 pages.

Sharp, "RNA Interference-2001", Genes & Development, 2001, 15(5), p. 485-490, 7 pages.

Scaringe, et al., "Novel RNA Synthesis Method Using 5'-O-Silyl-2'-O-orthoester Protecting Groups", J. Am. Chem. Soc., 1998, 120 (45), p. 11820-11821, 1 page.

Scaringe, "RNA Oligonucleotide Synthesis via 5'-Silyl-2'-Orthoester Chemistry", Methods, 2001, 23 (3), p. 206-217, 6 pages.

Takeuchi, et al., "Multiplex Reverse Transcription-PCR Screening for EML4-ALK Fusion Transcripts", Clin Cancer Res. 2008, 14(20), p. 6618-6624, 8 pages.

Daley and Baltimore, "Transformation of an Interleukin 3-dependent Hematopoietic Cell Line by the Chronic Myelogenous Leukemia-Specific P210 bcr/abl protein", Proc. Natl. Acad. Sci., USA 85 (23), (1988), p. 9312-9316, 5 pages.

Katayama, et al., "Mechanisms of Acquired Crizotinib Resistance in ALK-Rearranged Lung Cancers", Sci. Transl. Med, 2012, 4 (120) 120ra17, 25 pages.

Japanese Office Action dated Feb. 8, 2021, Application No. 2017-561206; English translation included, 8 pages.

Lee et al., "A Novel SND1-BRAF Fusion Confers Resistance to c-Met Inhibitor PF-04217903 in GTL 16 Cells though MAPK Activation", PLOS ONE, Jun. 2012, vol. 7, Issue 6, e39653, pp. 1-12.

Database GenBank [online], Accession No. AFN01665.01, "SND1-BRAF fusion [*Homo sapiens*]", Jul. 3, 2012, <https://www.ncbi.nlm.nih.gov/protein/AFN01665.1?report-genbank&log$=protalign&blast_rank=1&RID=0RFK8BT4013>, 2 pages.

\* cited by examiner

SEQUENCE LISTING

<160> NUMBER OF SEQ ID NOS: 10

<210> SEQ ID NO 1

<211> LENGTH: 2067
<212> TYPE: DNA
<213> ORGANISM: Homo sapiens
<220> FEATURE:
<221> NAME/KEY: CDS
<222> LOCATION: (132)..(1949)

<400> SEQUENCE: 1

| | |
|---|---:|
| gcgcgggcgc gcgcggcggc ggcgcgttcc gttccgggcc gaggctcgcg gcggaaaagt | 60 |
| tgcgggcat agacgagcgg ccccgggacg ggcagctagc gcgaccctga gccggcgccc | 120 |
| gtggtccggc c atg gac gac ctc gac gcc ctg ctg gcg gac ttg gag tct<br>           Met Asp Asp Leu Asp Ala Leu Leu Ala Asp Leu Glu Ser<br>            1               5                 10 | 170 |
| acc acc tcc cac atc tcc aaa cgg cct gtg ttc ttg tcg gag gag acc<br>Thr Thr Ser His Ile Ser Lys Arg Pro Val Phe Leu Ser Glu Glu Thr<br> 15                  20                  25 | 218 |
| ccc tac tca tac cca act gga aac cac aca tac cag gag att gcc gtg<br>Pro Tyr Ser Tyr Pro Thr Gly Asn His Thr Tyr Gln Glu Ile Ala Val<br>30                 35                  40                  45 | 266 |
| cca ccc ccc gtc ccc cca ccc ccg tcc agc gag gcc ctc aat ggc aca<br>Pro Pro Pro Val Pro Pro Pro Pro Ser Ser Glu Ala Leu Asn Gly Thr<br>                  50                  55                  60 | 314 |
| atc ctt gac ccc tta gac cag tgg cag ccc agc ggc tcc cga ttc atc<br>Ile Leu Asp Pro Leu Asp Gln Trp Gln Pro Ser Gly Ser Arg Phe Ile<br>             65                  70                  75 | 362 |
| cac cag cag cct cag tcc tca tca cct gtg tac ggc tcc agt gcc aaa<br>His Gln Gln Pro Gln Ser Ser Ser Pro Val Tyr Gly Ser Ser Ala Lys<br>                 80                  85                  90 | 410 |
| act tcc agt gtc tcc aac cct cag gac agt gtt ggc tct ccg tgc tcc<br>Thr Ser Ser Val Ser Asn Pro Gln Asp Ser Val Gly Ser Pro Cys Ser<br> 95                  100                105 | 458 |
| cga gtg ggt gag gag gag cac gtc tac agc ttc ccc aac aag cag aaa<br>Arg Val Gly Glu Glu Glu His Val Tyr Ser Phe Pro Asn Lys Gln Lys<br>110                 115                120               125 | 506 |
| tca gct gag cct tca ccc acc gta atg agc acg tcc ctg ggc agc aac<br>Ser Ala Glu Pro Ser Pro Thr Val Met Ser Thr Ser Leu Gly Ser Asn<br>                 130                135                140 | 554 |
| ctt tct gaa ctc gac cgc ctg ctg ctg gaa ctg aac gct gta cag cat<br>Leu Ser Glu Leu Asp Arg Leu Leu Leu Glu Leu Asn Ala Val Gln His<br>             145                150                155 | 602 |
| aac ccg cca ggc ttc cct gca gat gag gcc aac tca agc ccc ccg ctt<br>Asn Pro Pro Gly Phe Pro Ala Asp Glu Ala Asn Ser Ser Pro Pro Leu<br>                 160                165                170 | 650 |
| cct ggg gcc ctg agc ccc ctc tat ggt gtc cca gag act aac agc ccc<br>Pro Gly Ala Leu Ser Pro Leu Tyr Gly Val Pro Glu Thr Asn Ser Pro<br>175                 180                185 | 698 |
| ttg gga ggc aaa gct ggg ccc ctg acg aaa gag aag cct aag cgg aat<br>Leu Gly Gly Lys Ala Gly Pro Leu Thr Lys Glu Lys Pro Lys Arg Asn<br>190                 195                200               205 | 746 |
| ggg ggc cgg ggc ctg gag gac gtg cgg ccc agt gtg gag agt ctc ttg<br>Gly Gly Arg Gly Leu Glu Asp Val Arg Pro Ser Val Glu Ser Leu Leu<br>                 210                215                220 | 794 |
| gat gaa ctg gag agc tcc gtg ccc agc ccc gtc cct gcc atc act gtg<br>Asp Glu Leu Glu Ser Ser Val Pro Ser Pro Val Pro Ala Ile Thr Val<br>             225                230                235 | 842 |
| aac cag ggc gag atg agc agc ccg cag cgc gtc acc tcc acc caa cag<br>Asn Gln Gly Glu Met Ser Ser Pro Gln Arg Val Thr Ser Thr Gln Gln<br>                 240                245                250 | 890 |
| cag aca cgc atc tcg gcc tcc tct gcc acc agg gag ctg gac gag ctg<br>Gln Thr Arg Ile Ser Ala Ser Ser Ala Thr Arg Glu Leu Asp Glu Leu | 938 |

-continued

|  |  |  |  |  |  |  |  |  |  |  |  |  |  |  |  |  |
|---|---|---|---|---|---|---|---|---|---|---|---|---|---|---|---|---|
|  |  | 255 |  |  |  | 260 |  |  |  | 265 |  |  |  |  |  |  |
| atg | gct | tcg | ctg | tcg | gat | ttc | aag | aaa | aca | ctt | ggt | aga | cgg | gac | tcg | 986 |
| Met | Ala | Ser | Leu | Ser | Asp | Phe | Lys | Lys | Thr | Leu | Gly | Arg | Arg | Asp | Ser |  |
| 270 |  |  |  | 275 |  |  |  |  | 280 |  |  |  |  | 285 |  |  |
| agt | gat | gat | tgg | gag | att | cct | gat | ggg | cag | att | aca | gtg | gga | caa | aga | 1034 |
| Ser | Asp | Asp | Trp | Glu | Ile | Pro | Asp | Gly | Gln | Ile | Thr | Val | Gly | Gln | Arg |  |
|  |  |  |  | 290 |  |  |  |  | 295 |  |  |  |  | 300 |  |  |
| att | gga | tct | gga | tca | ttt | gga | aca | gtc | tac | aag | gga | aag | tgg | cat | ggt | 1082 |
| Ile | Gly | Ser | Gly | Ser | Phe | Gly | Thr | Val | Tyr | Lys | Gly | Lys | Trp | His | Gly |  |
|  |  |  | 305 |  |  |  |  | 310 |  |  |  |  | 315 |  |  |  |
| gat | gtg | gca | gtg | aaa | atg | ttg | aat | gtg | aca | gca | cct | aca | cct | cag | cag | 1130 |
| Asp | Val | Ala | Val | Lys | Met | Leu | Asn | Val | Thr | Ala | Pro | Thr | Pro | Gln | Gln |  |
|  |  | 320 |  |  |  |  | 325 |  |  |  |  | 330 |  |  |  |  |
| tta | caa | gcc | ttc | aaa | aat | gaa | gta | gga | gta | ctc | agg | aaa | aca | cga | cat | 1178 |
| Leu | Gln | Ala | Phe | Lys | Asn | Glu | Val | Gly | Val | Leu | Arg | Lys | Thr | Arg | His |  |
| 335 |  |  |  |  | 340 |  |  |  |  | 345 |  |  |  |  |  |  |
| gtg | aat | atc | cta | ctc | ttc | atg | ggc | tat | tcc | aca | aag | cca | caa | ctg | gct | 1226 |
| Val | Asn | Ile | Leu | Leu | Phe | Met | Gly | Tyr | Ser | Thr | Lys | Pro | Gln | Leu | Ala |  |
| 350 |  |  |  |  | 355 |  |  |  |  | 360 |  |  |  |  | 365 |  |
| att | gtt | acc | cag | tgg | tgt | gag | ggc | tcc | agc | ttg | tat | cac | cat | ctc | cat | 1274 |
| Ile | Val | Thr | Gln | Trp | Cys | Glu | Gly | Ser | Ser | Leu | Tyr | His | His | Leu | His |  |
|  |  |  | 370 |  |  |  |  | 375 |  |  |  |  | 380 |  |  |  |
| atc | att | gag | acc | aaa | ttt | gag | atg | atc | aaa | ctt | ata | gat | att | gca | cga | 1322 |
| Ile | Ile | Glu | Thr | Lys | Phe | Glu | Met | Ile | Lys | Leu | Ile | Asp | Ile | Ala | Arg |  |
|  |  | 385 |  |  |  |  | 390 |  |  |  |  | 395 |  |  |  |  |
| cag | act | gca | cag | ggc | atg | gat | tac | tta | cac | gcc | aag | tca | atc | atc | cac | 1370 |
| Gln | Thr | Ala | Gln | Gly | Met | Asp | Tyr | Leu | His | Ala | Lys | Ser | Ile | Ile | His |  |
|  |  |  | 400 |  |  |  |  | 405 |  |  |  |  | 410 |  |  |  |
| aga | gac | ctc | aag | agt | aat | aat | ata | ttt | ctt | cat | gaa | gac | ctc | aca | gta | 1418 |
| Arg | Asp | Leu | Lys | Ser | Asn | Asn | Ile | Phe | Leu | His | Glu | Asp | Leu | Thr | Val |  |
|  | 415 |  |  |  |  | 420 |  |  |  |  | 425 |  |  |  |  |  |
| aaa | ata | ggt | gat | ttt | ggt | cta | gct | aca | gtg | aaa | tct | cga | tgg | agt | ggg | 1466 |
| Lys | Ile | Gly | Asp | Phe | Gly | Leu | Ala | Thr | Val | Lys | Ser | Arg | Trp | Ser | Gly |  |
| 430 |  |  |  |  | 435 |  |  |  |  | 440 |  |  |  |  | 445 |  |
| tcc | cat | cag | ttt | gaa | cag | ttg | tct | gga | tcc | att | ttg | tgg | atg | gca | cca | 1514 |
| Ser | His | Gln | Phe | Glu | Gln | Leu | Ser | Gly | Ser | Ile | Leu | Trp | Met | Ala | Pro |  |
|  |  |  |  | 450 |  |  |  |  | 455 |  |  |  |  | 460 |  |  |
| gaa | gtc | atc | aga | atg | caa | gat | aaa | aat | cca | tac | agc | ttt | cag | tca | gat | 1562 |
| Glu | Val | Ile | Arg | Met | Gln | Asp | Lys | Asn | Pro | Tyr | Ser | Phe | Gln | Ser | Asp |  |
|  |  |  | 465 |  |  |  |  | 470 |  |  |  |  | 475 |  |  |  |
| gta | tat | gca | ttt | gga | att | gtt | ctg | tat | gaa | ttg | atg | act | gga | cag | tta | 1610 |
| Val | Tyr | Ala | Phe | Gly | Ile | Val | Leu | Tyr | Glu | Leu | Met | Thr | Gly | Gln | Leu |  |
|  |  | 480 |  |  |  |  | 485 |  |  |  |  | 490 |  |  |  |  |
| cct | tat | tca | aac | atc | aac | aac | agg | gac | cag | ata | att | ttt | atg | gtg | gga | 1658 |
| Pro | Tyr | Ser | Asn | Ile | Asn | Asn | Arg | Asp | Gln | Ile | Ile | Phe | Met | Val | Gly |  |
| 495 |  |  |  |  | 500 |  |  |  |  | 505 |  |  |  |  |  |  |
| cga | gga | tac | ctg | tct | cca | gat | ctc | agt | aag | gta | cgg | agt | aac | tgt | cca | 1706 |
| Arg | Gly | Tyr | Leu | Ser | Pro | Asp | Leu | Ser | Lys | Val | Arg | Ser | Asn | Cys | Pro |  |
| 510 |  |  |  |  | 515 |  |  |  |  | 520 |  |  |  |  | 525 |  |
| aaa | gcc | atg | aag | aga | tta | atg | gca | gag | tgc | ctc | aaa | aag | aaa | aga | gat | 1754 |
| Lys | Ala | Met | Lys | Arg | Leu | Met | Ala | Glu | Cys | Leu | Lys | Lys | Lys | Arg | Asp |  |
|  |  |  |  | 530 |  |  |  |  | 535 |  |  |  |  | 540 |  |  |
| gag | aga | cca | ctc | ttt | ccc | caa | att | ctc | gcc | tct | att | gag | ctg | ctg | gcc | 1802 |
| Glu | Arg | Pro | Leu | Phe | Pro | Gln | Ile | Leu | Ala | Ser | Ile | Glu | Leu | Leu | Ala |  |
|  |  |  | 545 |  |  |  |  | 550 |  |  |  |  | 555 |  |  |  |
| cgc | tca | ttg | cca | aaa | att | cac | cgc | agt | gca | tca | gaa | ccc | tcc | ttg | aat | 1850 |
| Arg | Ser | Leu | Pro | Lys | Ile | His | Arg | Ser | Ala | Ser | Glu | Pro | Ser | Leu | Asn |  |
|  |  | 560 |  |  |  |  | 565 |  |  |  |  | 570 |  |  |  |  |
| cgg | gct | ggt | ttc | caa | aca | gag | gat | ttt | agt | cta | tat | gct | tgt | gct | tct | 1898 |

-continued

```
Arg Ala Gly Phe Gln Thr Glu Asp Phe Ser Leu Tyr Ala Cys Ala Ser
            575                 580                 585 cca aaa aca ccc atc cag gca ggg gga tat ggt gcg ttt cct gtc cac      1946
Pro Lys Thr Pro Ile Gln Ala Gly Gly Tyr Gly Ala Phe Pro Val His
590                 595                 600                 605 tga aacaaatgag tgagagagtt caggagagta gcaacaaaag gaaataaat            1999 gaacatatgt ttgcttatat gttaaattga ataaaatact ctcttttttt ttaaggtgaa    2059
ccaaagaa                                                             2067

<210> SEQ ID NO 2
<211> LENGTH: 605
<212> TYPE: PRT
<213> ORGANISM: Homo sapiens

<400> SEQUENCE: 2

Met Asp Asp Leu Asp Ala Leu Leu Ala Asp Leu Glu Ser Thr Thr Ser
1               5                   10                  15

His Ile Ser Lys Arg Pro Val Phe Leu Ser Glu Glu Thr Pro Tyr Ser
            20                  25                  30

Tyr Pro Thr Gly Asn His Thr Tyr Gln Glu Ile Ala Val Pro Pro Pro
        35                  40                  45

Val Pro Pro Pro Ser Ser Glu Ala Leu Asn Gly Thr Ile Leu Asp
    50                  55                  60

Pro Leu Asp Gln Trp Gln Pro Ser Gly Ser Arg Phe Ile His Gln Gln
65                  70                  75                  80

Pro Gln Ser Ser Ser Pro Val Tyr Gly Ser Ser Ala Lys Thr Ser Ser
                85                  90                  95

Val Ser Asn Pro Gln Asp Ser Val Gly Ser Pro Cys Ser Arg Val Gly
            100                 105                 110

Glu Glu Glu His Val Tyr Ser Phe Pro Asn Lys Gln Lys Ser Ala Glu
        115                 120                 125

Pro Ser Pro Thr Val Met Ser Thr Ser Leu Gly Ser Asn Leu Ser Glu
    130                 135                 140

Leu Asp Arg Leu Leu Leu Glu Leu Asn Ala Val Gln His Asn Pro Pro
145                 150                 155                 160

Gly Phe Pro Ala Asp Glu Ala Asn Ser Ser Pro Pro Leu Pro Gly Ala
                165                 170                 175

Leu Ser Pro Leu Tyr Gly Val Pro Glu Thr Asn Ser Pro Leu Gly Gly
            180                 185                 190

Lys Ala Gly Pro Leu Thr Lys Glu Lys Pro Lys Arg Asn Gly Gly Arg
        195                 200                 205

Gly Leu Glu Asp Val Arg Pro Ser Val Glu Ser Leu Leu Asp Glu Leu
    210                 215                 220

Glu Ser Ser Val Pro Ser Pro Val Pro Ala Ile Thr Val Asn Gln Gly
225                 230                 235                 240

Glu Met Ser Ser Pro Gln Arg Val Thr Ser Thr Gln Gln Gln Thr Arg
                245                 250                 255

Ile Ser Ala Ser Ser Ala Thr Arg Glu Leu Asp Glu Leu Met Ala Ser
            260                 265                 270

Leu Ser Asp Phe Lys Lys Thr Leu Gly Arg Arg Asp Ser Ser Asp Asp
        275                 280                 285

Trp Glu Ile Pro Asp Gly Gln Ile Thr Val Gly Gln Arg Ile Gly Ser
    290                 295                 300

Gly Ser Phe Gly Thr Val Tyr Lys Gly Lys Trp His Gly Asp Val Ala
```

-continued

```
                305                 310                 315                 320
    Val Lys Met Leu Asn Val Thr Ala Pro Thr Pro Gln Gln Leu Gln Ala
                    325                 330                 335

Phe Lys Asn Glu Val Gly Val Leu Arg Lys Thr Arg His Val Asn Ile
                340                 345                 350

Leu Leu Phe Met Gly Tyr Ser Thr Lys Pro Gln Leu Ala Ile Val Thr
            355                 360                 365

Gln Trp Cys Glu Gly Ser Ser Leu Tyr His His Leu His Ile Ile Glu
        370                 375                 380

Thr Lys Phe Glu Met Ile Lys Leu Ile Asp Ile Ala Arg Gln Thr Ala
    385                 390                 395                 400

Gln Gly Met Asp Tyr Leu His Ala Lys Ser Ile Ile His Arg Asp Leu
                    405                 410                 415

Lys Ser Asn Asn Ile Phe Leu His Glu Asp Leu Thr Val Lys Ile Gly
                420                 425                 430

Asp Phe Gly Leu Ala Thr Val Lys Ser Arg Trp Ser Gly Ser His Gln
            435                 440                 445

Phe Glu Gln Leu Ser Gly Ser Ile Leu Trp Met Ala Pro Glu Val Ile
        450                 455                 460

Arg Met Gln Asp Lys Asn Pro Tyr Ser Phe Gln Ser Asp Val Tyr Ala
    465                 470                 475                 480

Phe Gly Ile Val Leu Tyr Glu Leu Met Thr Gly Gln Leu Pro Tyr Ser
                    485                 490                 495

Asn Ile Asn Asn Arg Asp Gln Ile Ile Phe Met Val Gly Arg Gly Tyr
                500                 505                 510

Leu Ser Pro Asp Leu Ser Lys Val Arg Ser Asn Cys Pro Lys Ala Met
            515                 520                 525

Lys Arg Leu Met Ala Glu Cys Leu Lys Lys Lys Arg Asp Glu Arg Pro
        530                 535                 540

Leu Phe Pro Gln Ile Leu Ala Ser Ile Glu Leu Leu Ala Arg Ser Leu
    545                 550                 555                 560

Pro Lys Ile His Arg Ser Ala Ser Glu Pro Ser Leu Asn Arg Ala Gly
                    565                 570                 575

Phe Gln Thr Glu Asp Phe Ser Leu Tyr Ala Cys Ala Ser Pro Lys Thr
                580                 585                 590

Pro Ile Gln Ala Gly Gly Tyr Gly Ala Phe Pro Val His
            595                 600                 605

<210> SEQ ID NO 3
<211> LENGTH: 1651
<212> TYPE: DNA
<213> ORGANISM: Homo sapiens
<220> FEATURE:
<221> NAME/KEY: CDS
<222> LOCATION: (271)..(1533)

<400> SEQUENCE: 3
gacgcgaatg acgctgcgcc agtcaggccg cagccccgct gcttggcccg tcgggcccgc      60
cttggccggc tcggcccgcc ccggccctc cctgcacggc ctcccgtgcg ccctgtcag      120 actgtgcgg ccggtcgcgc ggtgcgctct ccctccctgc ccgcagcctg agaggcgct      180 tcgtgctgca cacccccgcg ttcctgccgg caccgcgcct gccctctgcc gcgctccgcc      240
ctgccgccga ccgcacgccc gccgcgggac atg gca cac gca ccg gca cgc tgc      294
                                   Met Ala His Ala Pro Ala Arg Cys
                                     1               5
```

| | |
|---|---|
| ccc agc gcc cgg ggc tcc ggg gac ggc gag atg ggc aag ccc agg aac<br>Pro Ser Ala Arg Gly Ser Gly Asp Gly Glu Met Gly Lys Pro Arg Asn<br>    10                          15                        20 | 342 |
| gtg gcg ctc atc acc ggt atc aca ggc cag gac ttg att aga gac caa<br>Val Ala Leu Ile Thr Gly Ile Thr Gly Gln Asp Leu Ile Arg Asp Gln<br>25                       30                        35                        40 | 390 |
| gga ttt cgt ggt gat gga gga tca acc aca ggt ttg tct gct acc ccc<br>Gly Phe Arg Gly Asp Gly Gly Ser Thr Thr Gly Leu Ser Ala Thr Pro<br>                              45                        50                        55 | 438 |
| cct gcc tca tta cct ggc tca cta act aac gtg aaa gcc tta cag aaa<br>Pro Ala Ser Leu Pro Gly Ser Leu Thr Asn Val Lys Ala Leu Gln Lys<br>              60                        65                        70 | 486 |
| tct cca gga cct cag cga gaa agg aag tca tct tca tcc tca gaa gac<br>Ser Pro Gly Pro Gln Arg Glu Arg Lys Ser Ser Ser Ser Ser Glu Asp<br>          75                        80                        85 | 534 |
| agg aat cga atg aaa aca ctt ggt aga cgg gac tcg agt gat gat tgg<br>Arg Asn Arg Met Lys Thr Leu Gly Arg Arg Asp Ser Ser Asp Asp Trp<br>      90                        95                        100 | 582 |
| gag att cct gat ggg cag att aca gtg gga caa aga att gga tct gga<br>Glu Ile Pro Asp Gly Gln Ile Thr Val Gly Gln Arg Ile Gly Ser Gly<br>105                     110                      115                    120 | 630 |
| tca ttt gga aca gtc tac aag gga aag tgg cat ggt gat gtg gca gtg<br>Ser Phe Gly Thr Val Tyr Lys Gly Lys Trp His Gly Asp Val Ala Val<br>                          125                     130                    135 | 678 |
| aaa atg ttg aat gtg aca gca cct aca cct cag cag tta caa gcc ttc<br>Lys Met Leu Asn Val Thr Ala Pro Thr Pro Gln Gln Leu Gln Ala Phe<br>Lys            140                      145                      150 | 726 |
| aaa aat gaa gta gga gta ctc agg aaa aca cga cat gtg aat atc cta<br>Lys Asn Glu Val Gly Val Leu Arg Lys Thr Arg His Val Asn Ile Leu<br>              155                        160                    165 | 774 |
| ctc ttc atg ggc tat tcc aca aag cca caa ctg gct att gtt acc cag<br>Leu Phe Met Gly Tyr Ser Thr Lys Pro Gln Leu Ala Ile Val Thr Gln<br>170                     175                      180 | 822 |
| tgg tgt gag ggc tcc agc ttg tat cac cat ctc cat atc att gag acc<br>Trp Cys Glu Gly Ser Ser Leu Tyr His His Leu His Ile Ile Glu Thr<br>185                     190                      195                    200 | 870 |
| aaa ttt gag atg atc aaa ctt ata gat att gca cga cag act gca cag<br>Lys Phe Glu Met Ile Lys Leu Ile Asp Ile Ala Arg Gln Thr Ala Gln<br>                      205                      210                    215 | 918 |
| ggc atg gat tac tta cac gcc aag tca atc atc cac aga gac ctc aag<br>Gly Met Asp Tyr Leu His Ala Lys Ser Ile Ile His Arg Asp Leu Lys<br>              220                      225                    230 | 966 |
| agt aat aat ata ttt ctt cat gaa gac ctc aca gta aaa ata ggt gat<br>Ser Asn Asn Ile Phe Leu His Glu Asp Leu Thr Val Lys Ile Gly Asp<br>              235                      240                    245 | 1014 |
| ttt ggt cta gct aca gtg aaa tct cga tgg agt ggg tcc cat cag ttt<br>Phe Gly Leu Ala Thr Val Lys Ser Arg Trp Ser Gly Ser His Gln Phe<br>250                     255                      260 | 1062 |
| gaa cag ttg tct gga tcc att ttg tgg atg gca cca gaa gtc atc aga<br>Glu Gln Leu Ser Gly Ser Ile Leu Trp Met Ala Pro Glu Val Ile Arg<br>265                     270                      275                    280 | 1110 |
| atg caa gat aaa aat cca tac agc ttt cag tca gat gta tat gca ttt<br>Met Gln Asp Lys Asn Pro Tyr Ser Phe Gln Ser Asp Val Tyr Ala Phe<br>                      285                      290                    295 | 1158 |
| gga att gtt ctg tat gaa ttg atg act gga cag tta cct tat tca aac<br>Gly Ile Val Leu Tyr Glu Leu Met Thr Gly Gln Leu Pro Tyr Ser Asn<br>                      300                      305                    310 | 1206 |
| atc aac aac agg gac cag ata att ttt atg gtg gga cga gga tac ctg<br>Ile Asn Asn Arg Asp Gln Ile Ile Phe Met Val Gly Arg Gly Tyr Leu<br>              315                      320                    325 | 1254 |

```
tct cca gat ctc agt aag gta cgg agt aac tgt cca aaa gcc atg aag    1302
Ser Pro Asp Leu Ser Lys Val Arg Ser Asn Cys Pro Lys Ala Met Lys
    330                 335                 340 aga tta atg gca gag tgc ctc aaa aag aaa aga gat gag aga cca ctc    1350
Arg Leu Met Ala Glu Cys Leu Lys Lys Lys Arg Asp Glu Arg Pro Leu
345                 350                 355                 360 ttt ccc caa att ctc gcc tct att gag ctg ctg gcc cgc tca ttg cca    1398
Phe Pro Gln Ile Leu Ala Ser Ile Glu Leu Leu Ala Arg Ser Leu Pro
                365                 370                 375 aaa att cac cgc agt gca tca gaa ccc tcc ttg aat cgg gct ggt ttc    1446
Lys Ile His Arg Ser Ala Ser Glu Pro Ser Leu Asn Arg Ala Gly Phe
            380                 385                 390 caa aca gag gat ttt agt cta tat gct tgt gct tct cca aaa aca ccc    1494
Gln Thr Glu Asp Phe Ser Leu Tyr Ala Cys Ala Ser Pro Lys Thr Pro
        395                 400                 405 atc cag gca ggg gga tat ggt gcg ttt cct gtc cac tga aacaaatgag    1543
Ile Gln Ala Gly Gly Tyr Gly Ala Phe Pro Val His
    410                 415                 420 tgagagagtt caggagagta gcaacaaaag gaaataaat gaacatatgt ttgcttatat    1603
gttaaattga ataaaatact ctctttttt ttaaggtgaa ccaaagaa                1651

<210> SEQ ID NO 4
<211> LENGTH: 420
<212> TYPE: PRT
<213> ORGANISM: Homo sapiens

<400> SEQUENCE: 4

Met Ala His Ala Pro Ala Arg Cys Pro Ser Ala Arg Gly Ser Gly Asp
1               5                   10                  15

Gly Glu Met Gly Lys Pro Arg Asn Val Ala Leu Ile Thr Gly Ile Thr
            20                  25                  30

Gly Gln Asp Leu Ile Arg Asp Gln Gly Phe Arg Gly Asp Gly Gly Ser
        35                  40                  45

Thr Thr Gly Leu Ser Ala Thr Pro Pro Ala Ser Leu Pro Gly Ser Leu
    50                  55                  60

Thr Asn Val Lys Ala Leu Gln Lys Ser Pro Gly Pro Gln Arg Glu Arg
65                  70                  75                  80

Lys Ser Ser Ser Ser Glu Asp Arg Asn Arg Met Lys Thr Leu Gly
                85                  90                  95

Arg Arg Asp Ser Ser Asp Trp Glu Ile Pro Asp Gly Gln Ile Thr
            100                 105                 110

Val Gly Gln Arg Ile Gly Ser Gly Ser Phe Gly Thr Val Tyr Lys Gly
        115                 120                 125

Lys Trp His Gly Asp Val Ala Val Lys Met Leu Asn Val Thr Ala Pro
    130                 135                 140

Thr Pro Gln Gln Leu Gln Ala Phe Lys Asn Glu Val Gly Val Leu Arg
145                 150                 155                 160

Lys Thr Arg His Val Asn Ile Leu Leu Phe Met Gly Tyr Ser Thr Lys
                165                 170                 175

Pro Gln Leu Ala Ile Val Thr Gln Trp Cys Glu Gly Ser Ser Leu Tyr
            180                 185                 190

His His Leu His Ile Ile Glu Thr Lys Phe Glu Met Ile Lys Leu Ile
        195                 200                 205

Asp Ile Ala Arg Gln Thr Ala Gln Gly Met Asp Tyr Leu His Ala Lys
    210                 215                 220
```

-continued

```
Ser Ile Ile His Arg Asp Leu Lys Ser Asn Asn Ile Phe Leu His Glu
225                 230                 235                 240

Asp Leu Thr Val Lys Ile Gly Asp Phe Gly Leu Ala Thr Val Lys Ser
            245                 250                 255

Arg Trp Ser Gly Ser His Gln Phe Glu Gln Leu Ser Gly Ser Ile Leu
        260                 265                 270

Trp Met Ala Pro Glu Val Ile Arg Met Gln Asp Lys Asn Pro Tyr Ser
    275                 280                 285

Phe Gln Ser Asp Val Tyr Ala Phe Gly Ile Val Leu Tyr Glu Leu Met
290                 295                 300

Thr Gly Gln Leu Pro Tyr Ser Asn Ile Asn Asn Arg Asp Gln Ile Ile
305                 310                 315                 320

Phe Met Val Gly Arg Gly Tyr Leu Ser Pro Asp Leu Ser Lys Val Arg
            325                 330                 335

Ser Asn Cys Pro Lys Ala Met Lys Arg Leu Met Ala Glu Cys Leu Lys
        340                 345                 350

Lys Lys Arg Asp Glu Arg Pro Leu Phe Pro Gln Ile Leu Ala Ser Ile
    355                 360                 365

Glu Leu Leu Ala Arg Ser Leu Pro Lys Ile His Arg Ser Ala Ser Glu
370                 375                 380

Pro Ser Leu Asn Arg Ala Gly Phe Gln Thr Glu Asp Phe Ser Leu Tyr
385                 390                 395                 400

Ala Cys Ala Ser Pro Lys Thr Pro Ile Gln Ala Gly Gly Tyr Gly Ala
            405                 410                 415

Phe Pro Val His
            420

<210> SEQ ID NO 5
<211> LENGTH: 23
<212> TYPE: DNA
<213> ORGANISM: Artificial Sequence
<220> FEATURE:
<223> OTHER INFORMATION: PCR primer

<400> SEQUENCE: 5
cggaaaagtt gcggggcata gac                                        23

<210> SEQ ID NO 6
<211> LENGTH: 28
<212> TYPE: DNA
<213> ORGANISM: Artificial Sequence
<220> FEATURE:
<223> OTHER INFORMATION: PCR primer

<400> SEQUENCE: 6
ctctcactca tttgtttcag tggacagg                                   28

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
gcccctgtca gactgtggcg                                            20

<210> SEQ ID NO 8
<211> LENGTH: 19
<212> TYPE: DNA
```

```
<213> ORGANISM: Artificial Sequence
<220> FEATURE:
<223> OTHER INFORMATION: PCR primer

<400> SEQUENCE: 8
cctgctgctg gaactgaac                                                 19

<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
ctgccacatc accatgccac t                                              21

<210> SEQ ID NO 10
<211> LENGTH: 18
<212> TYPE: DNA
<213> ORGANISM: Artificial Sequence
<220> FEATURE:
<223> OTHER INFORMATION: PCR primer

<400> SEQUENCE: 10
gacatggcac acgcaccg                                                  18
```

FUSIONS AND METHOD FOR DETECTING SAME

TECHNICAL FIELD

The present invention relates to a novel fusion protein containing a BRAF kinase region or a fusion gene encoding the fusion protein, and a method for detecting the same.

The present invention also relates to a novel fusion protein containing at least a portion of PXN or GMDS or a fusion gene encoding the fusion protein, and a method for detecting the same.

BACKGROUND ART

As a result of chromosomal translocation, a fusion gene is produced by fusing originally separate genes. It has heretofore been known that: fusion genes containing a portion of a kinase gene as a constituent often play an essential role in carcinogenesis, as with BCR-ABL1 fusions in chronic myelogenous leukemia, EML4-ALK fusions in lung cancer, and ROS1 fusions in various cancers including lung cancer; and drugs inhibiting their functions serve as very effective anticancer agents (Non Patent Literature 1, Patent Literature 1, and Patent Literature 2).

For example, the emergence of a tyrosine kinase inhibitor crizotinib or erlotinib has motivated clinical findings on the relation of therapeutic effects on cancers to molecular diagnosis. The concept prevails that therapeutic drugs are administered after stratification of patients by molecular diagnostic screening of indicated patients.

BRAF (V-Raf murine sarcoma viral oncogene homolog B1) is serine/threonine kinase belonging to the Raf kinase family and is activated by binding to Ras-GTP (Non Patent Literature 2).

A plurality of cancers caused by BRAF fusion genes have heretofore been known. For example, KIAA1549-BRAF in brain tumor, SLC45A3-BRAF in prostate cancer, and AGTRAP-BRAF in stomach cancer are known (Non Patent Literatures 3 to 5). Fusions resulting from the rearrangement of the BRAF gene and a partner gene are constantly in a phosphorylated state of their kinase domains and continue to send signals to the MAP kinase/ERK pathway or the like, thereby leading to the malignant transformation of cells.

CITATION LIST

Patent Literature

Patent Literature 1: Japanese Patent No. 4303303
Patent Literature 2: WO2011/162295

Non Patent Literature

Non Patent Literature 1: Lugo, T G et al., Science. 247, 1079-1082 (1990).
Non Patent Literature 2: Stephens R M., Mol. Cell. Biol. 12, 3733-3742 (1992).
Non Patent Literature 3: Mark, W, ASCO Educational Book. e436-e440 (2014).
Non Patent Literature 4: Palanisamy, N., Nat. Med., 793-799 (2010).
Non Patent Literature 5: Mcmahon, M., Nat. Med., 749-750 (2010).

SUMMARY OF INVENTION

Technical Problem

An object of the present invention is to provide, on the basis of revealed fusions (fusion proteins and fusion genes) serving as novel causative factors of cancers, a method for detecting a fusion protein or a fusion gene encoding the fusion protein, a method for diagnosing a cancer by use of the detection method, a method for determining an applicable subject to a pharmaceutical composition for the treatment of a cancer, a kit and a primer set for the detection method, a method for screening for a substance that inhibits the activity and/or expression of a polypeptide which is the fusion protein, a pharmaceutical composition for the treatment of a cancer, containing the inhibiting substance, and a method for treating a cancer, comprising administering the pharmaceutical composition for the treatment of a cancer.

Solution to Problem

The present inventors have isolated and identified a novel fusion gene of a portion of PXN gene and a portion of kinase BRAF gene fused with each other, and a novel fusion gene of a portion of GMDS gene and a portion of kinase BRAF gene fused with each other, from samples obtained from colorectal cancer patients (Examples 1 to 3) and found that the fusion genes are present in samples from colorectal cancer patients (Examples 4 and 5).

On the basis of these findings, the present inventors provide methods for detecting BRAF fusion proteins or fusion genes encoding the fusion proteins, provide kits and primer sets therefor, enable determination of a cancer patient to be treated with a BRAF-inhibiting substance by detecting the fusion protein or the fusion gene encoding the fusion protein, and provide a method for treating a cancer, comprising the step of administering a BRAF-inhibiting substance to the cancer patient.

On the basis of these findings, the present inventors also provide a method for detecting a PXN or GMDS fusion protein or a fusion gene encoding the fusion protein, provide a kit and a primer set therefor, enable determination of a cancer patient to be treated with a PXN- or GMDS-inhibiting substance by detecting the fusion protein or the fusion gene encoding the fusion protein, and provide a method for treating a cancer, comprising the step of administering a PXN- or GMDS-inhibiting substance to the cancer patient.

The present invention relates to the following aspects:
[1] A method for detecting a BRAF fusion protein or a fusion gene encoding the fusion protein in a sample obtained from a subject.
[2] The detection method according to [1], wherein the detection method comprises the step of detecting the cleavage of the BRAF protein or the cleavage of a gene encoding the BRAF protein.
[3] The detection method according to [1], wherein the detection method comprises the step of detecting the presence of a fusion protein constituted from the BRAF protein with a partner protein different therefrom, or the presence of a fusion gene encoding the fusion protein.
[4] The detection method according to any of [1] to [3], wherein the fusion protein is a fusion protein of the BRAF protein with PXN or GMDS protein.

[5] The detection method according to any of [1] to [4], wherein the fusion protein is a polypeptide selected from the group consisting of the following polypeptides (a) to (d):
   (a) a polypeptide consisting of the amino acid sequence represented by SEQ ID NO: 2 (PXN-BRAF) or SEQ ID NO: 4 (GMDS-BRAF);
   (b) a polypeptide comprising the amino acid sequence represented by SEQ ID NO: 2 or SEQ ID NO: 4, and having tumorigenicity;
   (c) a polypeptide comprising an amino acid sequence with 80% or higher identity to the amino acid sequence represented by SEQ ID NO: 2 or SEQ ID NO: 4, and having tumorigenicity; and
   (d) a polypeptide comprising an amino acid sequence derived from the amino acid sequence represented by SEQ ID NO: 2 or SEQ ID NO: 4 by the deletion, substitution, and/or insertion of one or several amino acids, and having tumorigenicity.

[6] The detection method according to any of [1] to [5], wherein the BRAF fusion gene is a polynucleotide encoding a polypeptide according to [5].

[7] The detection method according to any of [1] to [6], wherein the fusion gene is DNA or mRNA.

[8] The detection method according to any of [1] to [7], wherein the sample is a digestive organ-derived sample.

[9] The detection method according to [8], wherein the digestive organ-derived sample is a gastrointestinal tract-derived sample.

[10] The detection method according to [8], wherein the digestive organ-derived sample is a lower gastrointestinal tract-derived sample.

[11] The detection method according to [8], wherein the digestive organ-derived sample is a large intestine-derived sample.

[12] A kit for the detection of a BRAF fusion gene, comprising a first probe capable of specifically recognizing a 5'-terminal genomic region of the BRAF gene, and a second probe capable of specifically recognizing a 3'-terminal genomic region of the BRAF gene.

[13] A kit for the detection of a BRAF fusion gene, comprising a first probe capable of specifically recognizing a 5'-terminal genomic region of a partner gene constituting the BRAF fusion gene together with the BRAF gene, and a second probe capable of specifically recognizing a 3'-terminal genomic region of the BRAF gene.

[14] A kit for the detection of a BRAF fusion gene, comprising sense and antisense primers designed to be capable of specifically amplifying a 5'-terminal region of a polynucleotide encoding the BRAF protein, and sense and antisense primers designed to be capable of specifically amplifying a 3'-terminal region of the polynucleotide.

[15] A kit for the detection of a PXN-BRAF or GMDS-BRAF fusion gene, comprising sense and antisense primers designed to be capable of specifically amplifying a polynucleotide encoding a polypeptide which is a fusion protein of the PXN or GMDS protein with the BRAF protein.

[16] A kit for the detection of a PXN-BRAF or GMDS-BRAF fusion gene, comprising sense and antisense primers designed to be capable of specifically amplifying a polynucleotide encoding a polypeptide selected from the group consisting of the following polypeptides (a) to (d):
   (a) a polypeptide consisting of the amino acid sequence represented by SEQ ID NO: 2 or SEQ ID NO: 4;
   (b) a polypeptide comprising the amino acid sequence represented by SEQ ID NO: 2 or SEQ ID NO: 4, and having tumorigenicity;
   (c) a polypeptide comprising an amino acid sequence with 80% or higher identity to the amino acid sequence represented by SEQ ID NO: 2 or SEQ ID NO: 4, and having tumorigenicity; and
   (d) a polypeptide comprising an amino acid sequence derived from the amino acid sequence represented by SEQ ID NO: 2 or SEQ ID NO: 4 by the deletion, substitution, and/or insertion of one or several amino acids, and having tumorigenicity.

[17] A kit for the detection of a BRAF fusion protein, comprising an anti-BRAF antibody capable of specifically recognizing a N-terminal region of the BRAF protein, and an anti-BRAF antibody capable of specifically recognizing a C-terminal region of the BRAF protein.

[18] A kit for the detection of a BRAF fusion protein, comprising an antibody specifically binding to a polypeptide in a N-terminal region of a partner protein constituting the BRAF fusion protein together with the BRAF protein, and an antibody specifically binding to a polypeptide in a C-terminal region of the BRAF protein.

[19] The kit according to [18], wherein the partner protein is PXN or GMDS protein.

[20] A primer set for detecting a fusion gene of PXN or GMDS gene with BRAF gene, comprising an antisense primer designed from a polynucleotide moiety encoding the BRAF protein, and a sense primer designed from a polynucleotide moiety encoding the PXN or GMDS protein, wherein the antisense primer consists of a nucleic acid molecule which anneals under stringent conditions to a polynucleotide according to [16], and the sense primer consists of a nucleic acid molecule which anneals under stringent conditions to a complementary strand of the polynucleotide according to [16].

[21] A primer set for detecting a fusion gene of PXN or GMDS gene with BRAF gene, comprising an antisense primer consisting of a nucleic acid molecule which anneals under stringent conditions to a polynucleotide consisting of the nucleotide sequence represented by SEQ ID NO: 1 or SEQ ID NO: 3, and a sense primer consisting of a nucleic acid molecule which anneals under stringent conditions to a complementary strand of the polynucleotide.

[22] A primer set comprising a sense primer and an antisense primer selected from the group consisting of the following sense and antisense primers (a) and (b):
   (a) a sense primer consisting of an oligonucleotide of at least 16 consecutive nucleotides arbitrarily selected from nucleotide positions 1 to 962 of SEQ ID NO: 1, and an antisense primer consisting of an oligonucleotide complementary to an oligonucleotide of at least 16 consecutive nucleotides arbitrarily selected from nucleotide positions 963 to 2067 of SEQ ID NO: 1; and
   (b) a sense primer consisting of an oligonucleotide of at least 16 consecutive nucleotides arbitrarily selected from nucleotide positions 1 to 372 of SEQ ID NO: 3, and an antisense primer consisting of an oligonucleotide complementary to an oligonucleotide of at least 16 consecutive nucleotides arbitrarily selected from nucleotide positions 373 to 1651 of SEQ ID NO: 3.

[23] A method for screening for a substance that inhibits the activity and/or expression of a polypeptide according to [5], comprising the steps of:
   (1) contacting the polypeptide or a cell expressing the polypeptide with a test substance;
   (2) analyzing whether or not to inhibit the activity and/or expression of the polypeptide; and
   (3) selecting the substance that inhibits the activity and/or expression of the polypeptide.

[24] The screening method according to [23], wherein the substance that inhibits the activity and/or expression of the polypeptide is a therapeutic agent for a BRAF fusion-positive cancer.
[25] The screening method according to [24], wherein the cancer is digestive organ cancer.
[26] The screening method according to [25], wherein the cancer is gastrointestinal cancer.
[27] The screening method according to [25], wherein the cancer is lower gastrointestinal cancer.
[28] The screening method according to [25], wherein the cancer is colorectal cancer.
[29] A pharmaceutical composition for the treatment of a BRAF fusion-positive cancer, comprising a substance that inhibits the activity and/or expression of a BRAF fusion protein.
[30] The pharmaceutical composition according to [29], wherein the substance that inhibits the activity and/or expression of a BRAF fusion protein is a kinase inhibitor.
[31] The pharmaceutical composition according to [29] or [30], wherein the BRAF fusion protein is a polypeptide according to [5].
[32] The pharmaceutical composition according to any of [29] to [31], wherein the cancer is digestive organ cancer.
[33] The pharmaceutical composition according to [32], wherein the cancer is gastrointestinal cancer.
[34] The pharmaceutical composition according to [32], wherein the cancer is lower gastrointestinal cancer.
[35] The pharmaceutical composition according to [32], wherein the cancer is colorectal cancer.
[36] A BRAF fusion protein.
[37] A fusion protein of PXN or GMDS with BRAF.
[38] The fusion protein according to [36], wherein the fusion protein is a polypeptide selected from the group consisting of the following polypeptides (a) to (d):
(a) a polypeptide consisting of the amino acid sequence represented by SEQ ID NO: 2 or SEQ ID NO: 4;
(b) a polypeptide comprising the amino acid sequence represented by SEQ ID NO: 2 or SEQ ID NO: 4, and having tumorigenicity;
(c) a polypeptide comprising an amino acid sequence with 80% or higher identity to the amino acid sequence represented by SEQ ID NO: 2 or SEQ ID NO: 4, and having tumorigenicity; and
(d) a polypeptide comprising an amino acid sequence derived from the amino acid sequence represented by SEQ ID NO: 2 or SEQ ID NO: 4 by the deletion, substitution, and/or insertion of one or several amino acids, and having tumorigenicity.
[39] A polynucleotide encoding a fusion protein according to any of [36] to [38].
[40] A vector comprising a polynucleotide according to [39].
[41] A cell transformed with a vector according to [40].
[42] A method for detecting a PXN or GMDS fusion protein or a fusion gene encoding the fusion protein in a sample obtained from a subject.
[43] The detection method according to [42], wherein the detection method comprises the step of detecting the cleavage of the PXN or GMDS protein or the cleavage of a gene encoding the PXN or GMDS protein.
[44] The detection method according to [42], wherein the detection method comprises the step of detecting the presence of a fusion protein constituted from the PXN or GMDS protein with a partner protein different therefrom or the presence of a fusion gene encoding the fusion protein.

[45] The detection method according to any of [42] to [44], wherein the fusion protein is a fusion protein of the PXN or GMDS protein with BRAF protein.
[46] The detection method according to any of [42] to [45], wherein the fusion protein is a polypeptide selected from the group consisting of the following polypeptides (a) to (d):
(a) a polypeptide consisting of the amino acid sequence represented by SEQ ID NO: 2 or SEQ ID NO: 4;
(b) a polypeptide comprising the amino acid sequence represented by SEQ ID NO: 2 or SEQ ID NO: 4, and having tumorigenicity;
(c) a polypeptide comprising an amino acid sequence with 80% or higher identity to the amino acid sequence represented by SEQ ID NO: 2 or SEQ ID NO: 4, and having tumorigenicity; and
(d) a polypeptide comprising an amino acid sequence derived from the amino acid sequence represented by SEQ ID NO: 2 or SEQ ID NO: 4 by the deletion, substitution, and/or insertion of one or several amino acids, and having tumorigenicity.
[47] The detection method according to any of [42] to [46], wherein the PXN or GMDS fusion gene is a polynucleotide encoding a polypeptide according to [46].
[48] The detection method according to any of [42] to [47], wherein the fusion gene is DNA or mRNA.
[49] The detection method according to any of [42] to [48], wherein the sample is a digestive organ-derived sample.
[50] The detection method according to [49], wherein the digestive organ-derived sample is a gastrointestinal tract-derived sample.
[51] The detection method according to [49], wherein the digestive organ-derived sample is a lower gastrointestinal tract-derived sample.
[52] The detection method according to [49], wherein the digestive organ-derived sample is a large intestine-derived sample.
[53] A kit for the detection of a PXN or GMDS fusion gene, comprising a first probe capable of specifically recognizing a 5'-terminal genomic region of the PXN or GMDS gene, and a second probe capable of specifically recognizing a 3'-terminal genomic region of the PXN or GMDS gene.
[54] A kit for the detection of a PXN or GMDS fusion gene, comprising a first probe capable of specifically recognizing a 3'-terminal genomic region of a partner gene constituting the PXN or GMDS fusion gene together with the PXN or GMDS gene, and a second probe capable of specifically recognizing a 5'-terminal genomic region of the PXN or GMDS gene.
[55] A kit for the detection of a PXN or GMDS fusion gene, comprising sense and antisense primers designed to be capable of specifically amplifying a 5'-terminal region of a polynucleotide encoding the PXN or GMDS protein, and sense and antisense primers designed to be capable of specifically amplifying a 3'-terminal region of the polynucleotide.
[56] A kit for the detection of a PXN-BRAF or GMDS-BRAF fusion gene, comprising sense and antisense primers designed to be capable of specifically amplifying a polynucleotide encoding a polypeptide which is a fusion protein of the PXN or GMDS protein with the BRAF protein.
[57] A kit for the detection of a PXN-BRAF or GMDS-BRAF fusion gene, comprising sense and antisense primers designed to be capable of specifically amplifying a polynucleotide encoding a polypeptide selected from the group consisting of the following polypeptides (a) to (d):

(a) a polypeptide consisting of the amino acid sequence represented by SEQ ID NO: 2 or SEQ ID NO: 4;
(b) a polypeptide comprising the amino acid sequence represented by SEQ ID NO: 2 or SEQ ID NO: 4, and having tumorigenicity;
(c) a polypeptide comprising an amino acid sequence with 80% or higher identity to the amino acid sequence represented by SEQ ID NO: 2 or SEQ ID NO: 4, and having tumorigenicity; and
(d) a polypeptide comprising an amino acid sequence derived from the amino acid sequence represented by SEQ ID NO: 2 or SEQ ID NO: 4 by the deletion, substitution, and/or insertion of one or several amino acids, and having tumorigenicity.

[58] A kit for the detection of a PXN or GMDS fusion protein, comprising an anti-PXN or anti-GMDS antibody capable of specifically recognizing a N-terminal region of the PXN or GMDS protein, and an anti-PXN or anti-GMDS antibody capable of specifically recognizing a C-terminal region of the PXN or GMDS protein.

[59] A kit for the detection of a PXN or GMDS fusion protein, comprising an antibody specifically binding to a polypeptide in a C-terminal region of a partner protein constituting the PXN or GMDS fusion protein together with the PXN or GMDS protein, and an antibody specifically binding to a polypeptide in a N-terminal region of the PXN or GMDS protein.

[60] The kit according to [59], wherein the partner protein is BRAF protein.

[61] A primer set for detecting a fusion gene of BRAF gene with PXN or GMDS gene, comprising an antisense primer designed from a polynucleotide moiety encoding the BRAF protein, and a sense primer designed from a polynucleotide moiety encoding the PXN or GMDS protein, wherein the antisense primer consists of a nucleic acid molecule which anneals under stringent conditions to a polynucleotide according to [57], and the sense primer consists of a nucleic acid molecule which anneals under stringent conditions to a complementary strand of the polynucleotide according to [57].

[62] A primer set for detecting a fusion gene of PXN or GMDS gene with BRAF gene, comprising an antisense primer consisting of a nucleic acid molecule which anneals under stringent conditions to a polynucleotide consisting of the nucleotide sequence represented by SEQ ID NO: 1 or SEQ ID NO: 3, and a sense primer consisting of a nucleic acid molecule which anneals under stringent conditions to a complementary strand of the polynucleotide.

[63] A primer set comprising a sense primer and an antisense primer selected from the group consisting of the following sense and antisense primers (a) and (b):
(a) a sense primer consisting of an oligonucleotide of at least 16 consecutive nucleotides arbitrarily selected from nucleotide positions 1 to 962 of SEQ ID NO: 1, and an antisense primer consisting of an oligonucleotide complementary to an oligonucleotide of at least 16 consecutive nucleotides arbitrarily selected from nucleotide positions 963 to 2067 of SEQ ID NO: 1; and
(b) a sense primer consisting of an oligonucleotide of at least 16 consecutive nucleotides arbitrarily selected from nucleotide positions 1 to 372 of SEQ ID NO: 3, and an antisense primer consisting of an oligonucleotide complementary to an oligonucleotide of at least 16 consecutive nucleotides arbitrarily selected from nucleotide positions 373 to 1651 of SEQ ID NO: 3.

[64] A method for screening for a substance that inhibits the activity and/or expression of a polypeptide according to [46], comprising the steps of:
(1) contacting the polypeptide or a cell expressing the polypeptide with a test substance;
(2) analyzing whether or not to inhibit the activity and/or expression of the polypeptide; and
(3) selecting the substance that inhibits the activity and/or expression of the polypeptide.

[65] The screening method according to [64], wherein the substance that inhibits the activity and/or expression of the polypeptide is a therapeutic agent for a PXN or GMDS fusion-positive cancer.

[66] The screening method according to [65], wherein the cancer is digestive organ cancer.

[67] The screening method according to [66], wherein the cancer is gastrointestinal cancer.

[68] The screening method according to [66], wherein the cancer is lower gastrointestinal cancer.

[69] The screening method according to [66], wherein the cancer is colorectal cancer.

[70] A pharmaceutical composition for the treatment of a PXN or GMDS fusion-positive cancer, comprising a substance that inhibits the activity and/or expression of a PXN or GMDS fusion protein.

[71] The pharmaceutical composition according to [70], wherein the substance that inhibits the activity and/or expression of a PXN or GMDS fusion protein is a kinase inhibitor.

[72] The pharmaceutical composition according to [70] or [71], wherein the PXN or GMDS fusion protein is a polypeptide according to [46].

[73] The pharmaceutical composition according to any of [70] to [72], wherein the cancer is digestive organ cancer.

[74] The pharmaceutical composition according to [73], wherein the cancer is gastrointestinal cancer.

[75] The pharmaceutical composition according to [73], wherein the cancer is lower gastrointestinal cancer.

[76] The pharmaceutical composition according to [73], wherein the cancer is colorectal cancer.

[77] A PXN or GMDS fusion protein.

[78] A fusion protein of PXN or GMDS with BRAF.

[79] The fusion protein according to [77], wherein the fusion protein is a polypeptide selected from the group consisting of the following polypeptides (a) to (d):
(a) a polypeptide consisting of the amino acid sequence represented by SEQ ID NO: 2 or SEQ ID NO: 4;
(b) a polypeptide comprising the amino acid sequence represented by SEQ ID NO: 2 or SEQ ID NO: 4, and having tumorigenicity;
(c) a polypeptide comprising an amino acid sequence with 80% or higher identity to the amino acid sequence represented by SEQ ID NO: 2 or SEQ ID NO: 4, and having tumorigenicity; and
(d) a polypeptide comprising an amino acid sequence derived from the amino acid sequence represented by SEQ ID NO: 2 or SEQ ID NO: 4 by the deletion, substitution, and/or insertion of one or several amino acids, and having tumorigenicity.

[80] A polynucleotide encoding a fusion protein according to any of [77] to [79].

[81] A vector comprising a polynucleotide according to [80].

[82] A cell transformed with a vector according to [81].

[83] A method for treating a BRAF fusion-positive cancer, wherein a substance that inhibits the activity and/or expression of a BRAF fusion protein is a kinase inhibitor.

[84] Use of a substance that inhibits the activity and/or expression of a BRAF fusion protein in the production of a pharmaceutical composition for the treatment of a BRAF fusion-positive cancer.

[85] A method for treating a PXN or GMDS fusion-positive cancer, wherein a substance that inhibits the activity and/or expression of a PXN or GMDS fusion protein is a kinase inhibitor.

[86] Use of a substance that inhibits the activity and/or expression of a PXN or GMDS fusion protein in the production of a pharmaceutical composition for the treatment of a PXN or GMDS fusion-positive cancer.

Advantageous Effects of Invention

The detection method of the present invention can be used as a method for detecting a BRAF fusion-positive cancer (particularly, digestive organ cancer). According to the detection method of the present invention, a BRAF fusion-positive cancer in a subject can be diagnosed, and further, whether or not to be an applicable subject to a BRAF-inhibiting substance can be determined. The kit and the primer set for detection of the present invention can be used in the detection method of the present invention. Furthermore, the inhibiting substance screening method of the present invention can screen for a substance effective for the treatment of a patient with the fusion-positive cancer. The substance obtained by the screening method can be used as an active ingredient in a pharmaceutical composition for the treatment of a BRAF fusion-positive cancer and can also be used in the treatment of a BRAF fusion-positive cancer.

The detection method of the present invention can be used as a method for detecting a PXN or GMDS fusion-positive cancer (particularly, digestive organ cancer). According to the detection method of the present invention, a PXN or GMDS fusion-positive cancer in a subject can be diagnosed, and further, whether or not to be an applicable subject to a PXN- or GMDS-inhibiting substance can be determined. The kit and the primer set for detection of the present invention can be used in the detection method of the present invention. Furthermore, the inhibiting substance screening method of the present invention can screen for a substance effective for the treatment of a patient with the fusion-positive cancer. The substance obtained by the screening method can be used as an active ingredient in a pharmaceutical composition for the treatment of a PXN or GMDS fusion-positive cancer and can also be used in the treatment of a PXN or GMDS fusion-positive cancer.

DESCRIPTION OF EMBODIMENTS

Figure 1:
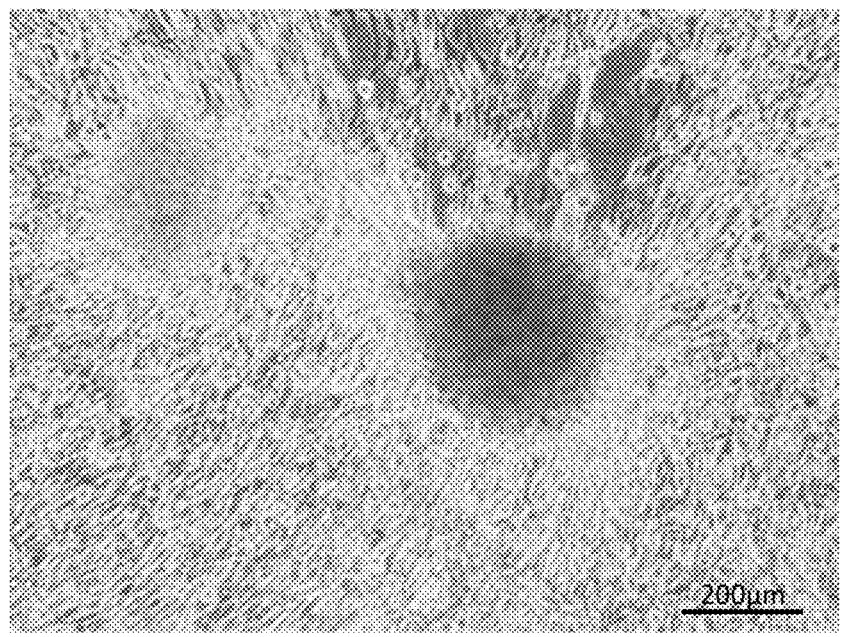
FIG. 1 is a microscopic photograph, instead of a drawing, showing the state of NIH3T3 fibroblasts transfected with a fusion gene PXN-BRAF and cultured for 7 days.
Figure 2:
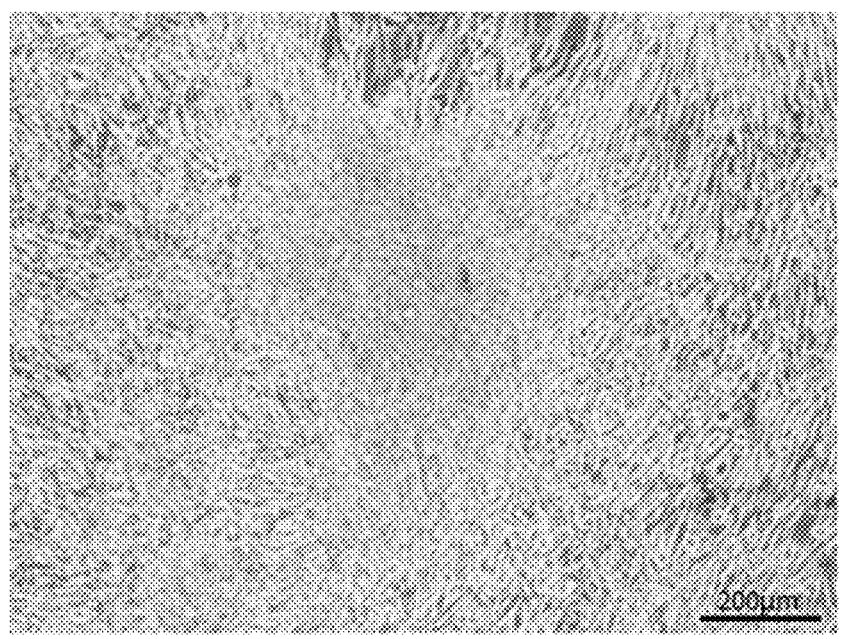
FIG. 2 is a microscopic photograph, instead of a drawing, showing the state of NIH3T3 fibroblasts transfected with a fusion gene GMDS-BRAF and cultured for 7 days.

Definition, Etc.

<Fusion Point>

In the present specification, the phrase "fusion point in a BRAF fusion gene" means a position at which a polynucleotide derived from the BRAF gene and a polynucleotide derived from a partner gene that constitutes the fusion gene together with the BRAF gene are joined with each other in the BRAF fusion gene.

In the present specification, the phrase "fusion point in a PXN or GMDS fusion gene" means a position at which a polynucleotide derived from the PXN or GMDS gene and a polynucleotide derived from a partner gene that constitutes the fusion gene together with the PXN or GMDS gene are joined with each other in the PXN or GMDS fusion gene.

When the BRAF fusion gene or the PXN or GMDS fusion gene is, for example, a PXN-BRAF fusion gene shown in SEQ ID NO: 1 (PXNex6-BRAFex11), the fusion point is a position (position 962/963) at which the 3'-terminal nucleotide (position 962) of the polynucleotide derived from the PXN gene and the 5'-terminal nucleotide (position 963) of the polynucleotide derived from the BRAF gene are joined with each other.

When the BRAF fusion gene or the PXN or GMDS fusion gene is a GMDS-BRAF fusion gene shown in SEQ ID NO: 3 (GMDSex1-BRAFex9), the fusion point is a position (position 372/373) at which the 3'-terminal nucleotide (position 372) of the polynucleotide derived from the GMDS gene and the 5'-terminal nucleotide (position 373) of the polynucleotide derived from the BRAF gene are joined with each other.

In the present specification, the phrase "fusion point in a BRAF fusion protein" means a position at which a polypeptide encoded by the polynucleotide derived from the BRAF gene and a polypeptide encoded by the polynucleotide derived from the partner gene that constitutes the fusion gene together with the BRAF gene are joined with each other in the BRAF fusion protein.

In the present specification, the phrase "fusion point in a PXN or GMDS fusion protein" means a position at which a polypeptide encoded by the polynucleotide derived from the PXN or GMDS gene and a polypeptide encoded by the polynucleotide derived from the partner gene that constitutes the fusion gene together with the PXN or GMDS gene are joined with each other in the PXN or GMDS fusion protein.

When the BRAF fusion protein or the PXN or GMDS fusion protein is, for example, a PXN-BRAF fusion protein shown in SEQ ID NO: 2, the fusion point is a position (position 277/278) at which the C-terminal amino acid (position 277) of the polypeptide derived from the PXN protein and the N-terminal amino acid (position 278) of the polypeptide derived from the BRAF protein are joined with each other.

When the BRAF fusion protein or the PXN or GMDS fusion protein is a GMDS-BRAF fusion protein shown in SEQ ID NO: 4, the fusion point is a position (position 34/35) at which the C-terminal amino acid (position 34) of the polypeptide derived from the GMDS protein and the N-terminal amino acid (position 35) of the polypeptide derived from the BRAF protein are joined with each other.

<Cleavage of BRAF Gene or BRAF Protein>

In the present specification, the phrase "cleavage of the BRAF gene" or "BRAF gene is cleaved" refers to a state where the continuity of the BRAF gene is lost due to the translocation or inversion, etc. of the gene, i.e., a state where the BRAF gene is separated into at least two polynucleotides, a polynucleotide containing a BRAF kinase region and another polynucleotide. The break point of the BRAF gene is not limited as long as a protein encoded by at least one of the polynucleotides resulting from the cleavage of the BRAF gene retains BRAF kinase activity.

Also, the phrase "cleavage of a partner gene different from the BRAF gene" or "partner gene different from the BRAF gene is cleaved" refers to a state where the continuity of the partner gene is lost due to the translocation or inversion, etc. of the gene, i.e., a state where the partner gene is separated into at least two polynucleotides.

In the present specification, the phrase "cleavage of the BRAF protein" or "BRAF protein is cleaved" refers to a state where the continuity of the BRAF protein is lost, i.e., a state where the BRAF protein is separated into at least two polypeptides, a polypeptide containing a BRAF kinase region and another polypeptide, on the basis of the cleaved state of the BRAF gene as mentioned above. The break point of the BRAF protein is not limited as long as at least one of the polypeptides resulting from the cleavage of the BRAF protein retains BRAF kinase activity.

Also, the phrase "cleavage of a partner protein different from the BRAF protein" or "partner protein different from the BRAF protein is cleaved" refers to a state where the continuity of the partner protein is lost, i.e., a state where the partner protein is separated into at least two polypeptides, on the basis of the cleaved state of the partner gene as mentioned above.

<Cleavage of PXN or GMDS Gene or PXN or GMDS Protein>

In the present specification, the phrase "cleavage of the PXN or GMDS gene" or "PXN or GMDS gene is cleaved" refers to a state where the continuity of the PXN or GMDS gene is lost due to the translocation or inversion, etc. of the gene. The break point of the PXN or GMDS gene is not limited as long as a protein encoded by a partner gene that constitutes the PXN or GMDS fusion gene together with the PXN or GMDS gene retains its function (e.g., kinase activity when this protein has a kinase domain).

Also, the phrase "cleavage of a partner gene different from the PXN or GMDS gene" or "partner gene different from the PXN or GMDS gene is cleaved" refers to a state where the continuity of the partner gene is lost due to the translocation or inversion, etc. of the gene, i.e., a state where the partner gene is separated into at least two polynucleotides.

In the present specification, the phrase "cleavage of the PXN or GMDS protein" or "PXN or GMDS protein is cleaved" refers to a state where the continuity of the PXN or GMDS protein is lost, i.e., a state where the PXN or GMDS protein is separated into at least two polypeptides, on the basis of the cleaved state of the PXN or GMDS gene as mentioned above. The break point of the PXN or GMDS protein is not limited as long as a partner protein that constitutes the PXN or GMDS fusion protein together with the PXN or GMDS protein retains its function (e.g., kinase activity when this protein has a kinase domain).

Also, the phrase "cleavage of a partner protein different from the PXN or GMDS protein" or "partner protein different from the PXN or GMDS protein is cleaved" refers to a state where the continuity of the partner protein is lost, i.e., a state where the partner protein is separated into at least two polypeptides, on the basis of the cleaved state of the partner gene as mentioned above.

<5'-Terminal Region/3'-Terminal Region and N-Terminal Region/C-Terminal Region>

The 5'-terminal region refers to, in the case of a fusion gene, a polynucleotide located on the 5'-terminal side with respect to the fusion point and, in the case of a wild-type gene (gene which is not a fusion gene), a polynucleotide located on the 5'-terminal side with respect to the break point when the wild-type gene constitutes a fusion gene. The 5'-terminal region may be a region in any of genomic DNA, mRNA, and cDNA and is also referred to as, for example, a 5'-terminal genomic region in the genomic DNA.

The 3'-terminal region refers to, in the case of a fusion gene, a polynucleotide located on the 3'-terminal side with respect to the fusion point and, in the case of a wild-type gene (gene which is not a fusion gene), a polynucleotide located on the 3'-terminal side with respect to the break point when the wild-type gene constitutes a fusion gene. The 3'-terminal region may be a region in any of genomic DNA, mRNA, and cDNA and is also referred to as, for example, a 3'-terminal genomic region in the genomic DNA.

The N-terminal region refers to, in the case of a fusion protein, a polypeptide located on the N-terminal side with respect to the fusion point and, in the case of a wild-type protein (protein which is not a fusion protein), a polypeptide located on the N-terminal side with respect to the break point when the wild-type protein constitutes a fusion protein.

The C-terminal region refers to, in the case of a fusion protein, a polypeptide located on the C-terminal side with respect to the fusion point and, in the case of a wild-type protein (protein which is not a fusion protein), a polypeptide located on the C-terminal side with respect to the break point when the wild-type protein constitutes a fusion protein.

For example, in a PXN-BRAF fusion gene shown in SEQ ID NO: 1 (PXNex6-BRAFex11), the 5'-terminal region is a polynucleotide consisting of a nucleotide sequence from positions 1 to 962, and the 3'-terminal region is a polynucleotide consisting of a nucleotide sequence from positions 963 to 2067. In a PXN-BRAF fusion protein shown in SEQ ID NO: 2, the N-terminal region is a polypeptide (amino acid positions 1 to 277 of SEQ ID NO: 2) encoded by CDS (nucleotide positions 132 to 962 of SEQ ID NO: 1) in the 5'-terminal region of the PXNex6-BRAFex11, and the C-terminal region is a polypeptide (amino acid positions 278 to 605 of SEQ ID NO: 2) encoded by CDS (nucleotide positions 963 to 1949 of SEQ ID NO: 1) in the 3'-terminal region of the PXNex6-BRAFex11.

In a GMDS-BRAF fusion gene shown in SEQ ID NO: 3 (GMDSex1-BRAFex9), the 5'-terminal region is a polynucleotide consisting of a nucleotide sequence from positions 1 to 372, and the 3'-terminal region is a polynucleotide consisting of a nucleotide sequence from positions 373 to 1651. In a GMDS-BRAF fusion protein shown in SEQ ID NO: 4, the N-terminal region is a polypeptide (amino acid positions 1 to 34 of SEQ ID NO: 4) encoded by CDS (nucleotide positions 271 to 372 of SEQ ID NO: 3) in the 5'-terminal region of the GMDSex1-BRAFex9, and the C-terminal region is a polypeptide (amino acid positions 35 to 420 of SEQ ID NO: 4) encoded by CDS (nucleotide positions 373 to 1533 of SEQ ID NO: 3) in the 3'-terminal region of the GMDSex1-BRAFex9.

<cDNA Reference Sequence>

In the present specification, ENST00000288602 for BRAF, ENST00000267257 for PXN, and ENST00000380815 for GMDS were used as cDNA reference sequences of the genes, and ENSP00000288602 for BRAF, ENSP00000267257 for PXN, and ENSP00000370194 for GMDS were used as amino acid reference sequences of the proteins.

<Stringent Conditions>

In the present specification, the term "stringent conditions" refers to conditions involving hybridization conditions of "5×SSPE, 5×Denhardt's solution, 0.5% SDS, 50% formamide, 200 µg/mL salmon sperm DNA, 42° C. overnight" and washing conditions of "0.5×SSC, 0.1% SDS, 42° C.". The term "more stringent conditions" refers to conditions involving hybridization conditions of "5×SSPE, 5×Denhardt's solution, 0.5% SDS, 50% formamide, 200 µg/mL salmon sperm DNA, 42° C., overnight" and washing conditions of "0.2×SSC, 0.1% SDS, 65° C.".

<Tumorigenicity>

Whether a polypeptide "has tumorigenicity" can be confirmed by a method known in the art, for example, a method described in Example 4 of WO2011/162295 or a method described in Example 6 mentioned later. Specifically, the confirmation method involves subcutaneously inoculating a host (3T3 fibroblasts) transfected with an expression plasmid for the polypeptide to a nude mouse and determining the presence or absence of tumor formation.

Sample for Use in Detection Method of Present Invention

<Target Organ>

The detection method according to the present invention can be suitably used in the detection of a cancer developed in a target organ. The test site (target organ) of a subject is not limited as long as the fusion according to the present invention is present therein. The test site is preferably a digestive organ, more preferably the gastrointestinal tract, further preferably the gastrointestine, still further preferably the lower gastrointestinal tract, particularly preferably the large intestine.

The histological type of the test site is not limited as long as the detection method according to the present invention is applicable thereto. The histological type may be a squamous epithelial tissue or may be a glandular tissue and is preferably a squamous epithelial tissue.

<Harvest from Subject>

In the detection method according to the present invention, a harvest from a subject (sample separated from an organism), specifically, an arbitrary harvested body fluid (preferably blood), a resected sample from an affected area in a subject, a biopsy sample or a swab sample, feces, urine, a gastrointestinal lavage fluid, or the like can be used as a sample obtained from a subject. The gastrointestinal lavage fluid may be a lavage fluid of the whole gastrointestinal tract or may be a lavage fluid of the gastrointestinal tract containing at least the test site, for example, a lavage fluid of the lower gastrointestinal tract or a lavage fluid of the large intestine. The sample obtained from a subject is preferably a sample containing cells of the test site in the target organ, more preferably a resected sample or a biopsy sample from the test site of the subject, in consideration of detection sensitivity.

<Preparation of Harvest>

The method for detecting a BRAF fusion gene or a BRAF fusion protein according to the present invention can be carried out by preparing a tissue section or a cell suspension, etc. of a sample obtained from a subject and detecting the BRAF fusion gene or the BRAF fusion protein in cells contained in the tissue section or the cell suspension by a technique well known to those skilled in the art. Alternatively, a lysate is prepared from the sample obtained from the subject mentioned above, and genes or proteins contained therein are extracted. In this extracted sample, the BRAF fusion gene or the BRAF fusion protein may be detected by a technique well known to those skilled in the art. The detection of the BRAF fusion gene may be the detection of genomic DNA of the BRAF fusion gene or may be the detection of mRNA which is a transcript of the genomic DNA or cDNA obtained with the mRNA as a template.

The method for detecting a PXN or GMDS fusion gene or a PXN or GMDS fusion protein according to the present invention can be carried out by preparing a tissue section or a cell suspension, etc. of a sample obtained from a subject and detecting the PXN or GMDS fusion gene or the PXN or GMDS fusion protein in cells contained in the tissue section or the cell suspension by a technique well known to those skilled in the art. Alternatively, a lysate is prepared from the sample obtained from the subject mentioned above, and genes or proteins contained therein are extracted. In this extracted sample, the PXN or GMDS fusion gene or the PXN or GMDS fusion protein may be detected by a technique well known to those skilled in the art. The detection of the PXN or GMDS fusion gene may be the detection of genomic DNA of the PXN or GMDS fusion gene or may be the detection of mRNA which is a transcript of the genomic DNA or cDNA obtained with the mRNA as a template.

Target to be Detected by Detection Method of Present Invention

The detection method of the present invention includes a method for detecting a BRAF fusion, i.e., a method for detecting a fusion protein containing a BRAF kinase region (also referred to as a "BRAF fusion protein"), or a method for detecting a fusion gene encoding the fusion protein (also referred to as a "BRAF fusion gene"), in a sample obtained from a subject.

The detection method of the present invention includes a method for detecting a PXN or GMDS fusion, i.e., a method for detecting a PXN or GMDS fusion protein, or a method for detecting a fusion gene encoding the fusion protein (also referred to as a "PXN or GMDS fusion gene"), in a sample obtained from a subject.

<BRAF Fusion: BRAF Fusion Protein and BRAF Fusion Gene>

The BRAF fusion according to the present invention includes a BRAF fusion protein and a BRAF fusion gene.

The BRAF fusion protein according to the present invention is a fusion polypeptide constituted from a polypeptide derived from the BRAF protein and a polypeptide derived from a partner protein different from the BRAF protein. The polypeptide derived from the BRAF protein is not particularly limited as long as the polypeptide comprises at least a polypeptide having a BRAF kinase region in the BRAF protein. The polypeptide derived from the partner protein different from the BRAF protein is not particularly limited as long as the polypeptide comprises at least a partial polypeptide of the partner protein.

The partner protein is not particularly limited as long as the BRAF fusion protein constituted by its fusion with a BRAF kinase domain-containing portion of the BRAF protein has tumorigenicity. It is preferred that the constituted BRAF fusion protein should constantly maintain BRAF kinase activation and thereby have tumorigenicity.

The BRAF fusion protein may comprise a third polypeptide which is neither the polypeptide derived from the BRAF protein nor the polypeptide derived from the partner protein different from the BRAF protein as long as the constituted BRAF fusion protein constantly maintains BRAF kinase activation and has tumorigenicity. The third polypeptide may be positioned at the N terminus of the BRAF fusion protein, may be positioned at the C terminus thereof, or may be positioned between the polypeptide derived from the BRAF protein and the polypeptide derived from the partner protein different from the BRAF protein.

The BRAF fusion protein is particularly preferably a fusion protein having PXN or GMDS protein as the partner protein. Specifically, the BRAF fusion protein is preferably a fusion protein of the PXN or GMDS protein with the BRAF protein (hereinafter, also referred to as a PXN-BRAF fusion protein or a GMDS-BRAF fusion protein, a PXN-BRAF or GMDS-BRAF fusion protein, or a PXN- or GMDS-BRAF fusion protein) constituted from a polypeptide derived from the BRAF protein, comprising at least a polypeptide having a BRAF kinase region, and a polypeptide derived from the PXN or GMDS protein, comprising at least a partial polypeptide of the PXN or GMDS protein.

<PXN or GMDS Fusion: PXN or GMDS Fusion Protein and PXN or GMDS Fusion Gene>

The PXN or GMDS fusion according to the present invention includes a PXN or GMDS fusion protein and a PXN or GMDS fusion gene.

The PXN or GMDS fusion protein according to the present invention is a fusion polypeptide constituted from a polypeptide derived from the PXN or GMDS protein and a polypeptide derived from a partner protein different from the PXN or GMDS protein. The polypeptide derived from the PXN or GMDS protein is not particularly limited as long as the polypeptide comprises at least a partial polypeptide of the PXN or GMDS protein. The polypeptide derived from the partner protein different from the PXN or GMDS protein is not particularly limited as long as the polypeptide comprises at least a partial polypeptide of the partner protein.

The partner protein is not particularly limited as long as the PXN or GMDS fusion protein constituted by its fusion with a portion of the PXN or GMDS protein has tumorigenicity. It is preferred that the PXN or GMDS fusion protein should constantly maintain the activation of a functional domain (preferably a kinase domain) carried by the partner protein and thereby have tumorigenicity.

The PXN or GMDS fusion protein may comprise a third polypeptide which is neither the polypeptide derived from the PXN or GMDS protein nor the polypeptide derived from the partner protein different from the PXN or GMDS protein as long as the constituted PXN or GMDS fusion protein constantly maintains the activation of a functional domain of the partner protein different from the PXN or GMDS protein by fusion with a portion of the PXN or GMDS protein and has tumorigenicity. The third polypeptide may be positioned at the N terminus of the PXN or GMDS fusion protein, may be positioned at the C terminus thereof, or may be positioned between the polypeptide derived from the PXN or GMDS protein and the polypeptide derived from the partner protein different from the PXN or GMDS protein.

The PXN or GMDS fusion protein is particularly preferably a fusion protein having BRAF protein as the partner protein. Specifically, the PXN or GMDS fusion protein is preferably a fusion protein of the PXN or GMDS protein with the BRAF protein (hereinafter, also referred to as a PXN-BRAF fusion protein or a GMDS-BRAF fusion protein, a PXN-BRAF or GMDS-BRAF fusion protein, or a PXN- or GMDS-BRAF fusion protein) constituted from a polypeptide derived from the PXN or GMDS protein, comprising at least a partial polypeptide of the PXN or GMDS protein, and at least a partial polypeptide of the BRAF protein, comprising at least a polypeptide having a BRAF kinase region.

The "PXN- or GMDS-BRAF fusion protein" is particularly preferably any of the following polypeptides (a) to (d):

(a) a polypeptide consisting of the amino acid sequence represented by SEQ ID NO: 2 (PXN-BRAF) or SEQ ID NO: 4 (GMDS-BRAF);

(b) a polypeptide comprising the amino acid sequence represented by SEQ ID NO: 2 or SEQ ID NO: 4, and having tumorigenicity;

(c) a polypeptide comprising an amino acid sequence with 80% or higher identity to the amino acid sequence represented by SEQ ID NO: 2 or SEQ ID NO: 4, and having tumorigenicity (hereinafter, referred to as a homologous polypeptide); and (d) a polypeptide comprising an amino acid sequence derived from the amino acid sequence represented by SEQ ID NO: 2 or SEQ ID NO: 4 by the deletion, substitution, and/or insertion of one or several amino acids, and having tumorigenicity (hereinafter, referred to as a functionally equivalent variant).

The amino acid sequence represented by SEQ ID NO: 2 is a sequence encoded by the nucleotide sequence represented by SEQ ID NO: 1, particularly, the nucleotide sequence represented by nucleotide positions 132 to 1949 (CDS) of SEQ ID NO: 1. The nucleotide sequence represented by SEQ ID NO: 1 consists of a nucleotide sequence having the 5'-UTR sequence of the PXN gene, start codon ATG to exon 6 of the PXN gene, exon 11 to stop codon at exon 18 of the BRAF gene, and the 3'-UTR sequence of the BRAF gene. In the nucleotide sequence represented by SEQ ID NO: 1, the sequence from nucleotide positions 1 to 962 is derived from the PXN gene, and the sequence from nucleotide positions 963 to 2067 is derived from the BRAF gene. In the present specification, the polypeptide consisting of the amino acid sequence represented by SEQ ID NO: 2, and a polynucleotide consisting of a nucleotide sequence encoding this polypeptide (including a polynucleotide consisting of the nucleotide sequence represented by SEQ ID NO: 1) are collectively referred to as a PXNex6-BRAFex11 fusion (or simply PXNex6-BRAFex11).

The amino acid sequence represented by SEQ ID NO: 4 is a sequence encoded by the nucleotide sequence represented by SEQ ID NO: 3, particularly, the nucleotide sequence represented by nucleotide positions 271 to 1533 (CDS) of SEQ ID NO: 3. The nucleotide sequence represented by SEQ ID NO: 3 consists of a nucleotide sequence having the 5'-UTR sequence of the GMDS gene, start codon ATG to exon 1 of the GMDS gene, exon 9 to stop codon at exon 18 of the BRAF gene, and the 3'-UTR sequence of the BRAF gene. In the nucleotide sequence represented by SEQ ID NO: 3, the sequence from nucleotide positions 1 to 372 is derived from the GMDS gene, and the sequence from nucleotide positions 373 to 1651 is derived from the BRAF gene. In the present specification, the polypeptide consisting of the amino acid sequence represented by SEQ ID NO: 4, and a polynucleotide consisting of a nucleotide sequence encoding this polypeptide (including a polynucleotide consisting of the nucleotide sequence represented by SEQ ID NO: 3) are collectively referred to as a GMDSex1-BRAFex9 fusion (or simply GMDSex1-BRAFex9).

In the "functionally equivalent variant", the number of amino acids that can be substituted, deleted, and/or inserted is 1 to several, preferably 1 to 10, more preferably 1 to 7, most preferably 1 to 5.

The "homologous polypeptide" is a "polypeptide comprising an amino acid sequence with 80% or higher identity to the amino acid sequence represented by SEQ ID NO: 2 or SEQ ID NO: 4, and having tumorigenicity", preferably a polypeptide comprising an amino acid sequence with the identity of preferably 90% or higher, more preferably 95% or higher, further preferably 98% or higher. The "polypeptide comprising an amino acid sequence with 80% or higher identity to the amino acid sequence represented by SEQ ID NO: 2 or SEQ ID NO: 4, and having tumorigenicity" includes a polypeptide that exhibits the identity described above and a polypeptide having at least one substitution, deletion, and/or insertion (preferably substitution) (homologous polypeptide in the narrow sense) and a polypeptide having 100% identity.

In the present specification, the "identity" means a value Identity obtained using parameters provided as defaults by NEEDLE program (J Mol Biol 1970; 48: 443-453) search. The parameters are as follows:

Gap penalty=10
Extend penalty=0.5
Matrix=EBLOSUM62

The BRAF fusion gene according to the present invention is a polynucleotide encoding the BRAF fusion protein. In the present specification, the BRAF fusion protein and the BRAF fusion gene are also collectively referred to as a "BRAF fusion".

The PXN or GMDS fusion gene according to the present invention is a polynucleotide encoding the PXN or GMDS fusion protein. Specifically, the PXN fusion gene is a polynucleotide encoding the PXN fusion protein, and the GMDS fusion gene is a polynucleotide encoding the GMDS fusion protein. In the present specification, the PXN or GMDS fusion protein and the PXN or GMDS fusion gene are also collectively referred to as a "PXN or GMDS fusion".

The BRAF fusion according to the present invention is preferably a PXNex6-BRAFex11 fusion variant or a GMDSex1-BRAFex9 fusion variant. Particularly, the BRAF fusion protein according to the present invention is preferably a PXNex6-BRAFex11 fusion protein variant or a GMDSex1-BRAFex9 fusion protein variant. Also, the BRAF fusion gene according to the present invention is preferably a PXNex6-BRAFex11 fusion gene variant or a GMDSex1-BRAFex9 fusion gene variant.

The PXN or GMDS fusion according to the present invention is preferably a PXNex6-BRAFex11 fusion variant or a GMDSex1-BRAFex9 fusion variant. Particularly, the PXN or GMDS fusion protein according to the present invention is preferably a PXNex6-BRAFex11 fusion protein variant or a GMDSex1-BRAFex9 fusion protein variant. Also, the PXN or GMDS fusion gene according to the present invention is preferably a PXNex6-BRAFex11 fusion gene variant or a GMDSex1-BRAFex9 fusion gene variant.

Aspect of Detection Method of Present Invention
(Methods for Detecting Fusion Protein and Fusion Gene)

The detection method of the present invention includes a detection method comprising the step of detecting the cleavage of the BRAF protein or the cleavage of the BRAF gene encoding the BRAF protein in a sample obtained from a subject, and a detection method comprising the step of detecting the presence of a fusion protein constituted from the BRAF protein with a partner protein different from the BRAF protein, or the presence of a fusion gene encoding the fusion protein in a sample obtained from a subject.

The detection method of the present invention includes a detection method comprising the step of detecting the cleavage of the PXN or GMDS protein or the cleavage of the PXN or GMDS gene encoding the PXN or GMDS protein in a sample obtained from a subject, and a detection method comprising the step of detecting the presence of a fusion protein constituted from the PXN or GMDS protein with a partner protein different from the PXN or GMDS protein, or the presence of a fusion gene encoding the fusion protein in a sample obtained from a subject.

<Aspect of Detecting BRAF Fusion Gene>

Hereinafter, aspects of detecting the BRAF fusion gene will be described, but are not limited to those described below.

The detection of a particular region in a gene in each aspect given below may be performed using a probe or a primer designed on the basis of a nucleotide sequence analyzed in advance or may be performed by sequencing, regardless of the examples thereof.

[Aspect (1) of Detecting BRAF Fusion Gene]

<Aspect (1-a) of Detecting BRAF Fusion Gene>

The BRAF gene is cleaved into two or more polynucleotides when the BRAF fusion gene is constituted. On the basis of this event, in one aspect of detecting the BRAF fusion gene, the BRAF fusion gene can be detected by detecting the state where the BRAF gene is cleaved, i.e., the continuity between the 5'-terminal region of the BRAF gene and the 3'-terminal region of the BRAF gene is lost.

Specifically, the BRAF fusion gene can be detected, for example, by using a first probe which specifically hybridizes to the 5'-terminal region of the BRAF gene and a second probe which specifically hybridizes to the 3'-terminal region of the BRAF gene and detecting these two gene regions located distant from each other on the chromosome.

The BRAF fusion gene may be detected by confirming the state where the partner gene constituting the fusion gene by its fusion with the polynucleotide derived from the BRAF gene is cleaved, according to the method described above.

<Aspect (1-b) of Detecting BRAF Fusion Gene>

In an alternative aspect, the BRAF fusion gene can be detected by specifically detecting the respective expression levels of the 5'-terminal region and the 3'-terminal region of the BRAF gene and determining the ratio between the expression levels. Specifically, the BRAF fusion gene can be detected, for example, when the expression level of the 5'-terminal region of the BRAF gene and the expression level of the 3'-terminal region of the BRAF gene are different from each other.

Alternatively, the BRAF fusion gene may be detected by confirming this as to the partner gene, different from the BRAF gene, constituting the BRAF fusion gene together with the BRAF gene, according to the method described above.

<Aspect (1-c) of Detecting BRAF Fusion Gene>

In an alternative aspect, the process of formation of the BRAF fusion gene may involve the duplication of at least a portion of the BRAF gene or the partner gene different from the BRAF gene. In other words, the BRAF fusion gene may be constituted from a duplicated polynucleotide derived from the BRAF gene and a duplicated polynucleotide derived from the partner gene, different from the BRAF gene, constituting the BRAF fusion gene together with the BRAF gene. In this case, the BRAF fusion gene can be detected by detecting the duplication of the polynucleotide derived from the BRAF gene or the polynucleotide derived from the partner gene.

[Aspect (2) of Detecting BRAF Fusion Gene]

The BRAF fusion gene is constituted by the fusion between the polynucleotide derived from the BRAF gene and the polynucleotide derived from the partner gene different from the BRAF gene. On the basis of this event, in one aspect of detecting the BRAF fusion gene, the BRAF fusion gene can be detected by detecting a fusion polynucleotide consecutively comprising at least a portion of the polynucleotide derived from the BRAF gene and at least a portion of the polynucleotide derived from the gene different from the BRAF gene in the BRAF fusion gene.

Specifically, the BRAF fusion gene can be detected, for example, by using a first probe which specifically hybridizes to the 5'-terminal region of the polynucleotide derived from the partner gene different from the BRAF gene, and a second probe which specifically hybridizes to the 3'-terminal region of the polynucleotide derived from the BRAF gene, and detecting these two gene regions located in proximity on the chromosome. When the partner gene different from the BRAF gene is PXN or GMDS gene, i.e., the BRAF fusion gene is a PXN- or GMDS-BRAF fusion gene, the first probe can employ a probe which specifically hybridizes to the 5'-terminal region of the polynucleotide derived from the PXN or GMDS gene.

[Aspect (3) of Detecting BRAF Fusion Gene]

The BRAF fusion gene is constituted by the fusion at the fusion point between the polynucleotide derived from the BRAF gene and the polynucleotide derived from the partner gene different from the BRAF gene. On the basis of this event, in one aspect of detecting the BRAF fusion gene, the BRAF fusion gene can be detected by detecting a fusion polynucleotide consecutively comprising at least a portion of the polynucleotide derived from the BRAF gene and at least a portion of the polynucleotide derived from the partner gene different from the BRAF gene in the BRAF fusion gene, and containing the fusion point.

Specifically, the BRAF fusion gene can be detected, for example, by performing PCR reaction using a first primer which specifically anneals to the 5'-terminal region of the polynucleotide derived from the partner gene different from the BRAF gene, and a second primer which specifically anneals to the 3'-terminal region of the polynucleotide derived from the BRAF gene, and confirming that a predetermined PCR product that indicates the presence of the fusion point is obtained.

<Aspect of Detecting BRAF Fusion Protein>

Hereinafter, aspects of detecting the BRAF fusion protein will be described, but are not limited to those described below.

[Aspect (1) of Detecting BRAF Fusion Protein]

<Aspect (1-a) of Detecting BRAF Fusion Protein>

The BRAF protein encoded by the BRAF gene is also cleaved when the BRAF fusion gene is constituted. On the basis of this event, in an aspect of detecting the BRAF fusion protein, the BRAF fusion protein can be detected by detecting the state where the BRAF protein is cleaved, i.e., the continuity between the N-terminal region and the C-terminal region of the BRAF protein is lost.

Specifically, the BRAF fusion protein can be detected, for example, by using a first antibody specifically binding to the N-terminal region of the BRAF protein, and a second antibody specifically binding to the C-terminal region of the BRAF protein, and confirming that these two regions are absent in the same protein.

Alternatively, the BRAF fusion protein may be detected by confirming the state where the partner protein, different from the BRAF protein, constituting the fusion protein together with the BRAF protein is cleaved, according to the method described above.

<Aspect (1-b) of Detecting BRAF Fusion Protein>

In an alternative aspect, the BRAF fusion protein can be detected by specifically detecting the respective expression levels of the N-terminal region and the C-terminal region of the BRAF protein and determining the ratio between the expression levels. Specifically, the BRAF fusion protein can be detected, for example, by using, as an index, the difference between the expression level of the N-terminal region of the BRAF protein and the expression level of the C-terminal region of the BRAF protein.

Alternatively, the BRAF fusion protein may be detected by confirming this as to the partner protein, different from the BRAF protein, constituting the BRAF fusion protein together with the BRAF protein, according to the method described above.

[Aspect (2) of Detecting BRAF Fusion Protein]

The BRAF fusion protein is constituted by the fusion between the polypeptide derived from the BRAF protein and the polypeptide derived from the partner protein different from the BRAF protein. On the basis of this event, in one aspect of detecting the BRAF fusion protein, the BRAF fusion protein can be detected by detecting a fusion polypeptide consecutively comprising at least a portion of the polypeptide derived from the BRAF protein and at least a portion of the polypeptide derived from the partner protein in the BRAF fusion protein.

Specifically, the BRAF fusion protein can be detected, for example, by using a first antibody specifically binding to the N-terminal region of the partner protein different from the BRAF protein, and a second antibody specifically binding to the C-terminal region of the BRAF protein, and confirming that these two regions are present in the same protein.

[Aspect (3) of Detecting BRAF Fusion Protein]

The BRAF fusion protein is constituted by the fusion at the fusion point between the polypeptide derived from the BRAF protein and the polypeptide derived from the partner protein different from the BRAF protein. On the basis of this event, in one aspect of detecting the BRAF fusion protein, the BRAF fusion protein can be detected by detecting a fusion polypeptide consecutively comprising at least a portion of the polypeptide derived from the BRAF protein and at least a portion of the polypeptide derived from the partner protein in the BRAF fusion protein, and containing the fusion point.

Specifically, the BRAF fusion protein can be detected, for example, by immunoassay using an antibody specifically recognizing a polypeptide containing the fusion point of the BRAF fusion protein.

[Aspect (4) of Detecting BRAF Fusion Protein]

In one aspect of detecting the BRAF fusion protein, the BRAF fusion protein can be detected by using the activity of the BRAF fusion protein as an index.

Specifically, the BRAF fusion protein can be detected, for example, by using a substance having inhibitory activity against wild-type BRAF protein to inhibit the activity of the wild-type BRAF protein, then measuring the kinase activity of the BRAF protein, and using, as an index, higher activity than that in the absence of the BRAF fusion protein (in the presence of only the wild-type BRAF protein). For the measurement of the kinase activity of the BRAF protein, a method well known to those skilled in the art can be appropriately selected, and, for example, the phosphorylated state of a molecule that undergoes phosphorylation by BRAF may be detected.

The detection of the BRAF fusion protein may be performed by using, as an index, the presence of a full-length polypeptide constituting the BRAF fusion protein or the presence of a polypeptide constituting a portion of the BRAF fusion protein, and is not limited as long as the presence of the BRAF fusion protein can be confirmed.

<Aspect of Detecting PXN or GMDS Fusion Gene>

Hereinafter, aspects of detecting the PXN or GMDS fusion gene will be described, but are not limited to those described below.

The detection of a particular region in a gene in each aspect given below may be performed using a probe or a primer designed on the basis of a nucleotide sequence analyzed in advance or may be performed by sequencing, regardless of the examples thereof.

[Aspect (1) of Detecting PXN or GMDS Fusion Gene]

<Aspect (1-a) of Detecting PXN or GMDS Fusion Gene>

The PXN or GMDS gene is cleaved into two or more polynucleotides when the PXN or GMDS fusion gene is constituted. On the basis of this event, in one aspect of detecting the PXN or GMDS fusion gene, the PXN or GMDS fusion gene can be detected by detecting the state where the PXN or GMDS gene is cleaved, i.e., the continuity between the 5'-terminal region of the PXN or GMDS gene and the 3'-terminal region of the PXN or GMDS gene is lost.

Specifically, the PXN or GMDS fusion gene can be detected, for example, by using a first probe which specifically hybridizes to the 5'-terminal region of the PXN or GMDS gene and a second probe which specifically hybridizes to the 3'-terminal region of the PXN or GMDS gene and detecting these two gene regions located distant from each other on the chromosome.

The PXN or GMDS fusion gene may be detected by confirming the state where the partner gene constituting the fusion gene by its fusion with the polynucleotide derived from the PXN or GMDS gene is cleaved, according to the method described above.

<Aspect (1-b) of Detecting PXN or GMDS Fusion Gene>

In an alternative aspect, the PXN or GMDS fusion gene can be detected by specifically detecting the respective expression levels of the 5'-terminal region and the 3'-terminal region of the PXN or GMDS gene and determining the ratio between the expression levels. Specifically, the PXN or GMDS fusion gene can be detected, for example, when the expression level of the 5'-terminal region of the PXN or GMDS gene and the expression level of the 3'-terminal region of the PXN or GMDS gene are different from each other.

Alternatively, the PXN or GMDS fusion gene may be detected by confirming this as to the partner gene, different from the PXN or GMDS gene, constituting the PXN or GMDS fusion gene together with the PXN or GMDS gene, according to the method described above.

<Aspect (1-c) of Detecting PXN or GMDS Fusion Gene>

The process of formation of the PXN or GMDS fusion gene may involve the duplication of at least a portion of the PXN or GMDS gene or the partner gene different from the PXN or GMDS gene. In other words, the PXN or GMDS fusion gene may be constituted from a duplicated polynucleotide derived from the PXN or GMDS gene and a duplicated polynucleotide derived from the partner gene, different from the PXN or GMDS gene, constituting the PXN or GMDS fusion gene together with the PXN or GMDS gene. In this case, in an alternative aspect, the PXN or GMDS fusion gene can be detected by detecting the duplication of the polynucleotide derived from the PXN or GMDS gene or the polynucleotide derived from the partner gene.

[Aspect (2) of Detecting PXN or GMDS Fusion Gene]

The PXN or GMDS fusion gene is constituted by the fusion between the polynucleotide derived from the PXN or GMDS gene and the polynucleotide derived from the partner gene different from the PXN or GMDS gene. On the basis of this event, in one aspect of detecting the PXN or GMDS fusion gene, the PXN or GMDS fusion gene can be detected by detecting a fusion polynucleotide consecutively comprising at least a portion of the polynucleotide derived from the PXN or GMDS gene and at least a portion of the polynucleotide derived from the gene different from the PXN or GMDS gene in the PXN or GMDS fusion gene.

Specifically, the PXN or GMDS fusion gene can be detected, for example, by using a first probe which specifically hybridizes to the 5'-terminal region of the polynucleotide derived from the PXN or GMDS gene, and a second probe which specifically hybridizes to the 3'-terminal region of the polynucleotide derived from the partner gene different from the PXN or GMDS gene, and detecting these two gene regions located in proximity on the chromosome. When the partner gene different from the PXN or GMDS gene is BRAF gene, i.e., the PXN or GMDS fusion gene is a PXN- or GMDS-BRAF fusion gene, the second probe can employ a probe which specifically hybridizes to the 3'-terminal region of the polynucleotide derived from the BRAF gene.

[Aspect (3) of Detecting PXN or GMDS Fusion Gene]

The PXN or GMDS fusion gene is constituted by the fusion at the fusion point between the polynucleotide derived from the PXN or GMDS gene and the polynucleotide derived from the partner gene different from the PXN or GMDS gene. On the basis of this event, in one aspect of detecting the PXN or GMDS fusion gene, the PXN or GMDS fusion gene can be detected by detecting a fusion polynucleotide consecutively comprising at least a portion of the polynucleotide derived from the PXN or GMDS gene and at least a portion of the polynucleotide derived from the partner gene different from the PXN or GMDS gene in the PXN or GMDS fusion gene, and containing the fusion point.

Specifically, the PXN or GMDS fusion gene can be detected, for example, by performing PCR reaction using a first primer which specifically anneals to the 5'-terminal region of the polynucleotide derived from the PXN or GMDS gene, and a second primer which specifically anneals to the 3'-terminal region of the polynucleotide derived from the partner gene different from the PXN or GMDS gene, and confirming that a predetermined PCR product that indicates the presence of the fusion point is obtained.

<Aspect of Detecting PXN or GMDS Fusion Protein>

Hereinafter, aspects of detecting the PXN or GMDS fusion protein will be described, but are not limited to those described below.

[Aspect (1) of Detecting PXN or GMDS Fusion Protein]

<Aspect (1-a) of Detecting PXN or GMDS Fusion Protein>

The PXN or GMDS protein encoded by the PXN or GMDS gene is also cleaved when the PXN or GMDS fusion gene is constituted. On the basis of this event, in an aspect of detecting the PXN or GMDS fusion protein, the PXN or GMDS fusion protein can be detected by detecting the state where the PXN or GMDS protein is cleaved, i.e., the continuity between the N-terminal region and the C-terminal region of the PXN or GMDS protein is lost.

Specifically, the PXN or GMDS fusion protein can be detected, for example, by using a first antibody specifically binding to the N-terminal region of the PXN or GMDS protein, and a second antibody specifically binding to the C-terminal region of the PXN or GMDS protein, and confirming that these two regions are absent in the same protein.

Alternatively, the PXN or GMDS fusion protein may be detected by confirming the state where the partner protein, different from the PXN or GMDS protein, constituting the fusion protein together with the PXN or GMDS protein is cleaved, according to the method described above.

<Aspect (1-b) of Detecting PXN or GMDS Fusion Protein>

In an alternative aspect, the PXN or GMDS fusion protein can be detected by specifically detecting the respective expression levels of the N-terminal region and the C-terminal region of the PXN or GMDS protein and determining the ratio between the expression levels. Specifically, the PXN or GMDS fusion protein can be detected, for example, by using, as an index, the difference between the expression level of the N-terminal region of the PXN or GMDS protein and the expression level of the C-terminal region of the PXN or GMDS protein.

Alternatively, the PXN or GMDS fusion protein may be detected by confirming this as to the partner protein, different from the PXN or GMDS protein, constituting the PXN or GMDS fusion protein together with the PXN or GMDS protein, according to the method described above.

[Aspect (2) of Detecting PXN or GMDS Fusion Protein]

The PXN or GMDS fusion protein is constituted by the fusion between the polypeptide derived from the PXN or GMDS protein and the polypeptide derived from the partner protein different from the PXN or GMDS protein. On the basis of this event, in one aspect of detecting the PXN or GMDS fusion protein, the PXN or GMDS fusion protein can be detected by detecting a fusion polypeptide consecutively comprising at least a portion of the polypeptide derived from the PXN or GMDS protein and at least a portion of the polypeptide derived from the partner protein in the PXN or GMDS fusion protein.

Specifically, the PXN or GMDS fusion protein can be detected, for example, by using a first antibody specifically binding to the N-terminal region of the PXN or GMDS protein, and a second antibody specifically binding to the C-terminal region of the partner protein different from the PXN or GMDS protein, and confirming that these two regions are present in the same protein.

[Aspect (3) of Detecting PXN or GMDS Fusion Protein]

The PXN or GMDS fusion protein is constituted by the fusion at the fusion point between the polypeptide derived from the PXN or GMDS protein and the polypeptide derived from the partner protein different from the PXN or GMDS protein. On the basis of this event, in one aspect of detecting the PXN or GMDS fusion protein, the PXN or GMDS fusion protein can be detected by detecting a fusion polypeptide consecutively comprising at least a portion of the polypeptide derived from the PXN or GMDS protein and at least a portion of the polypeptide derived from the partner protein in the PXN or GMDS fusion protein, and containing the fusion point.

Specifically, the PXN or GMDS fusion protein can be detected, for example, by immunoassay using an antibody specifically recognizing a polypeptide containing the fusion point of the PXN or GMDS fusion protein.

[Aspect (4) of Detecting PXN or GMDS Fusion Protein]

In one aspect of detecting the PXN or GMDS fusion protein, the PXN or GMDS fusion protein can be detected by using the activity of the PXN or GMDS fusion protein as an index.

Specifically, when the partner protein, different from the PXN or GMDS protein, constituting the fusion protein together with the PXN or GMDS protein is a protein having enzymatic activity, the PXN or GMDS fusion protein can be detected, for example, by using, as an index, higher enzymatic activity concerned than that in the absence of the PXN or GMDS fusion protein (in the presence of only the wild-type PXN or GMDS protein). For the measurement of the enzymatic activity, a method well known to those skilled in the art can be appropriately selected. When the partner protein is, for example, a protein having kinase activity (preferably BRAF protein), the phosphorylated state of a molecule that undergoes phosphorylation by PXN or GMDS fusion protein may be detected.

The detection of the PXN or GMDS fusion protein may be performed by using, as an index, the presence of a full-length polypeptide constituting the PXN or GMDS fusion protein or the presence of a polypeptide constituting a portion of the PXN or GMDS fusion protein, and is not limited as long as the presence of the PXN or GMDS fusion protein can be confirmed.

Technique for Use in Detection Method

Hereinafter, each step and each detection technique for the detection of the BRAF fusion gene (genomic DNA, mRNA, or cDNA), the detection of the PXN or GMDS fusion gene (genomic DNA, mRNA, or cDNA), the detection of the BRAF fusion protein, and the detection of the PXN or GMDS fusion protein will be described in more detail, but are not limited to those described below.

In the case of extracting a gene (genomic DNA or mRNA) or a protein from a sample obtained from a subject or in the case of preparing a tissue section or a cell suspension, etc. therefrom, a suitable technique for detecting the BRAF fusion gene or the PXN or GMDS fusion gene, or the BRAF fusion protein or the PXN or GMDS fusion protein in the prepared sample can be appropriately selected by those skilled in the art.

<Detection of Fusion Gene>

The detection of the BRAF fusion gene or the PXN or GMDS fusion gene may be the detection of genomic DNA of the BRAF fusion gene or the PXN or GMDS fusion gene, the detection of mRNA which is a transcript of the genomic DNA, or the detection of cDNA obtained with the mRNA as a template.

Any technique well known to those skilled in the art for use in gene detection, such as a hybridization technique using a probe (nucleic acid probe, etc.) which hybridizes to at least a portion of the BRAF fusion gene or the PXN or GMDS fusion gene, or a gene amplification technique using a primer which anneals to at least a portion of the BRAF fusion gene or the PXN or GMDS fusion gene, and applied techniques based on these techniques can be used as a technique of detecting the BRAF fusion gene (genomic DNA or mRNA) or the PXN or GMDS fusion gene (genomic DNA or mRNA) in a sample obtained from a subject.

Specifically, any technique may be used, such as PCR, LCR (ligase chain reaction), SDA (strand displacement amplification), NASBA (nucleic acid sequence-based amplification), ICAN (isothermal and chimeric primer-initiated amplification of nucleic acids), LAMP (loop-mediated isothermal amplification), TMA (Gen-Probe's TMA system), in situ hybridization, microarray, Northern hybridization, Southern hybridization, dot blot, RNA protection, DNA sequencing, or RNA sequencing.

[Detection of Genomic DNA]

An in situ hybridization technique can be suitably used in the detection of the genomic DNA. The detection using the in situ hybridization technique can be carried out according to, for example, FISH known in the art. Alternatively, this detection can be carried out by fusion assay based on chromogenic in situ hybridization (CISH) and silver in situ hybridization (SISH) in combination. Preferably, the genomic DNA can be detected by FISH split assay or FISH fusion assay described in detail below.

Alternatively, a DNA sequencing technique can be suitably used in the detection of the genomic DNA. The sequencing may employ a conventional sequencer based on the Sanger method and preferably employs a next-generation sequencer in consideration of analysis efficiency (see e.g., Metzker M L, Nat Rev Genet. 2010 January; 11 (1): 31-46). Examples of the next-generation sequencer can include MiSeq/HiSeq from Illumina, Inc., SOLiD System from Life Technologies Corp., and 454 Sequencing System (GS FLX+/GS Junior) from F. Hoffmann-La Roche, Ltd. In the sequencing, the efficiency of analysis can be improved by enriching a region likely to contain the fusion gene using a sequencing capture technique or the like. Examples of the sequencing capture technique can include Roche Nimble-Gen from F. Hoffmann-La Roche, Ltd. and Sure Select from Agilent Technologies, Inc.

Hereinafter, typical methods for detecting the genomic DNA will be illustrated, but are not limited to those described below.

<FISH Split Assay>

In the FISH split assay for the BRAF fusion gene, a fluorescently labeled polynucleotide covering the 5'-terminal genomic region of the BRAF gene, and a labeled (with another fluorescent dye) polynucleotide covering the 3'-terminal genomic region of this gene are used in combination as probes for detection. A color resulting from the overlap of two signals (e.g., yellow in the case of using a red fluorescent dye and a green fluorescent dye) is detected under normal conditions (in the case of wild-type BRAF gene), because the two gene regions (5'-terminal region and 3'-terminal region of each gene) are located in proximity. On the other hand, separate and distant signals (e.g., red and green) derived from the two types of fluorescent dyes are detected when the gene is cleaved into two regions due to translocation or inversion. Thus, the FISH split assay detects the presence of the BRAF fusion gene by detecting the 5'-terminal genomic region and the 3'-terminal genomic region of the BRAF gene located distant from each other on the chromosome.

In the FISH split assay for the PXN or GMDS fusion gene, a fluorescently labeled polynucleotide covering the 5'-terminal genomic region of the PXN or GMDS gene, and a labeled (with another fluorescent dye) polynucleotide covering the 3'-terminal genomic region of this gene are used in combination as probes for detection. A color resulting from the overlap of two signals (e.g., yellow in the case of using a red fluorescent dye and a green fluorescent dye) is detected under normal conditions (in the case of wild-type PXN or GMDS gene), because the two gene regions (5'-terminal region and 3'-terminal region of each gene) are located in proximity. On the other hand, separate and distant signals (e.g., red and green) derived from the two types of fluorescent dyes are detected when the gene is cleaved into two regions due to translocation or inversion. Thus, the FISH split assay detects the presence of the PXN or GMDS fusion gene by detecting the 5'-terminal genomic region and the 3'-terminal genomic region of the PXN or GMDS gene located distant from each other on the chromosome.

When the BRAF fusion gene or the PXN or GMDS fusion gene is a PXN- or GMDS-BRAF fusion gene, the PXN- or GMDS-BRAF fusion gene can be detected by using a fluorescently labeled polynucleotide covering the 5'-terminal genomic region of the PXN or GMDS gene, and a labeled (with another fluorescent dye) polynucleotide covering the 3'-terminal genomic region of this gene, or a fluorescently labeled polynucleotide covering the 5'-terminal genomic region of the BRAF gene, and a labeled (with another fluorescent dye) polynucleotide covering the 3'-terminal genomic region of this gene, in combination as probes for detection.

<FISH Fusion Assay>

In the FISH fusion assay for the BRAF fusion gene, when the BRAF fusion gene is, for example, a PXN- or GMDS-BRAF fusion gene, a fluorescently labeled polynucleotide covering the 3'-terminal genomic region of the BRAF gene, and a labeled (with another fluorescent dye) polynucleotide covering the 5'-terminal genomic region of the PXN or GMDS gene can be used in combination as probes for detection. Separate and distant signals (e.g., red and green) derived from the two types of fluorescent dyes are detected under normal conditions (in the case of wild-type BRAF gene). On the other hand, a color resulting from the overlap of two signals (e.g., yellow) is detected when the two gene regions are located in proximity due to translocation or inversion.

In the FISH fusion assay for the PXN or GMDS fusion gene, when the PXN or GMDS fusion gene is, for example, a PXN- or GMDS-BRAF fusion gene, a fluorescently labeled polynucleotide covering the 3'-terminal genomic region of the BRAF gene, and a labeled (with another fluorescent dye) polynucleotide covering the 5'-terminal genomic region of the PXN or GMDS gene can be used in combination as probes for detection. Separate and distant signals (e.g., red and green) derived from the two types of fluorescent dyes are detected under normal conditions (in the case of wild-type PXN or GMDS gene). On the other hand, a color resulting from the overlap of two signals (e.g., yellow) is detected when the two gene regions are located in proximity due to translocation or inversion.

<Detection of Gene Duplication by Use of FISH>

In the detection of gene duplication associated with BRAF fusion gene construction, when the BRAF fusion gene is, for example, a PXN- or GMDS-BRAF fusion gene, a fluorescently labeled polynucleotide covering at least a portion of the 3'-terminal genomic region of the BRAF gene can be used as a probe for detection. The BRAF fusion gene can be detected by detecting the obtainment of a stronger signal, for example, a signal two or more times stronger, than that in the presence of only wild-type BRAF gene.

The BRAF fusion gene may be detected by the method described above using a probe for the detection of the 5'-terminal genomic region of the partner gene (e.g., the PXN or GMDS gene when the BRAF fusion gene is a PXN- or GMDS-BRAF fusion gene) constituting the fusion gene by its fusion with the polynucleotide derived from the BRAF gene.

In the detection of gene duplication associated with PXN or GMDS fusion gene construction, when the PXN or GMDS fusion gene is, for example, a PXN- or GMDS-BRAF fusion gene, a fluorescently labeled polynucleotide covering at least a portion of the 5'-terminal genomic region of the PXN or GMDS gene can be used as a probe for detection. The PXN or GMDS fusion gene can be detected by detecting the obtainment of a stronger signal, for example, a signal two or more times stronger, than that in the presence of only wild-type PXN or GMDS gene.

The PXN or GMDS fusion gene may be detected by the method described above using a probe for the detection of the 3'-terminal genomic region of the partner gene (e.g., the BRAF gene when the PXN or GMDS fusion gene is a PXN or GMDS-BRAF fusion gene) constituting the fusion gene by its fusion with the polynucleotide derived from the PXN or GMDS gene.

<Detection of Gene Duplication by Use of CGH Array Analysis>

The gene duplication associated with BRAF fusion gene construction or PXN or GMDS fusion gene construction can be detected by comparative genomic hybridization (CGH) array analysis (e.g., Agilent CGH/CNV Array Analysis; Agilent Technologies, Inc.).

<Detection of Gene Duplication Using Next-Generation Sequencer>

The gene duplication associated with BRAF fusion gene construction or PXN or GMDS fusion gene construction can be detected using a next-generation sequencer. Specifically, in analysis using the next-generation sequencer, the BRAF fusion gene or the PXN or GMDS fusion gene can be detected by detecting high coverage of a gene duplication site (high redundancy of this site when the sequence of the DNA fragment to be analyzed is annotated with a reference sequence).

<Probe for Use in Detection (for Genome)>

The probe for use in hybridization for detecting the BRAF fusion gene is preferably a probe which hybridizes under stringent conditions (preferably under more stringent conditions) to at least partial nucleotides of the BRAF fusion gene or a complementary strand thereof.

In the case of detecting, for example, genomic DNA of the BRAF fusion gene containing the fusion point, a probe comprising a nucleic acid molecule of at least 32 consecutive bases consisting of 16 upstream and 16 downstream bases flanking the fusion point of the BRAF fusion gene, or a complementary strand thereof may be used.

The probe for use in hybridization for detecting the PXN or GMDS fusion gene is preferably a probe which hybridizes under stringent conditions (preferably under more stringent conditions) to at least partial nucleotides of the PXN or GMDS fusion gene or a complementary strand thereof.

In the case of detecting, for example, genomic DNA of the PXN or GMDS fusion gene containing the fusion point, a probe comprising a nucleic acid molecule of at least 32 consecutive bases consisting of 16 upstream and 16 downstream bases flanking the fusion point of the PXN or GMDS fusion gene, or a complementary strand thereof may be used.

When the BRAF fusion gene or the PXN or GMDS fusion gene is, for example, a PXN- or GMDS-BRAF fusion gene, a first probe capable of specifically recognizing the 5'-terminal genomic region of any one of the BRAF gene and the PXN or GMDS gene, and a second probe capable of specifically recognizing the 3'-terminal genomic region of the other gene (preferably a first probe capable of specifically recognizing the 3'-terminal genomic region of the BRAF gene, and a second probe capable of specifically recognizing the 5'-terminal genomic region of the PXN or GMDS gene) can be used in combination as the probes capable of using in the FISH fusion assay.

Meanwhile, when the BRAF fusion gene or the PXN or GMDS fusion gene is, for example, a PXN- or GMDS-BRAF fusion gene, a first probe capable of specifically recognizing the 5'-terminal genomic region of the BRAF gene, and a second probe capable of specifically recognizing the 3'-terminal genomic region of the BRAF gene, or a first probe capable of specifically recognizing the 5'-terminal genomic region of the PXN or GMDS gene, and a second probe capable of specifically recognizing the 3'-terminal genomic region of the PXN or GMDS gene (preferably a first probe capable of specifically recognizing the 5'-terminal genomic region of the BRAF gene, and a second probe capable of specifically recognizing the 3'-terminal genomic region of the BRAF gene) can be used in combination as the probes capable of using in the FISH split assay.

[Detection of mRNA]

The detection of the mRNA may be performed by analyzing the mRNA itself by Northern hybridization or the like or may be performed by analyzing complementary DNA (cDNA) synthesized with the mRNA as a template by a method well known to those skilled in the art.

A sequencing technique can be suitably used in the detection of the RNA. The sequencing preferably employs a next-generation sequencer (see e.g., Metzker M L, Nat Rev Genet. 2010 January; 11 (1): 31-46) in consideration of analysis efficiency. Examples of the next-generation sequencer can include MiSeq/HiSeq from Illumina, Inc., SOLiD System from Life Technologies Corp., and 454 Sequencing System (GS FLX+/GS Junior) from F. Hoffmann-La Roche, Ltd. In the sequencing, the efficiency of analysis can be improved by enriching a region likely to contain the fusion gene using a gene amplification reaction method mentioned later, a sequencing capture technique or the like. Examples of the sequencing capture technique can include Roche NimbleGen from F. Hoffmann-La Roche, Ltd. and Sure Select from Agilent Technologies, Inc.

<Detection by Gene Amplification Reaction Method>

The mRNA can be detected by a gene amplification reaction method using a primer designed to be capable of specifically amplifying at least a partial polynucleotide of the BRAF fusion gene or the PXN or GMDS fusion gene to be detected. Hereinafter, typical methods for detecting the mRNA will be illustrated, but are not limited to those described below.

==PCR==

For example, in PCR, the PCR product is analyzed by agarose gel electrophoresis, and whether or not an amplified fragment having the size of interest is obtained can be confirmed by ethidium bromide staining or the like. The obtainment of the amplified fragment having the size of interest means the presence of the BRAF fusion gene or the PXN or GMDS fusion gene in the sample obtained from a subject. In this way, the BRAF fusion gene or the PXN or GMDS fusion gene can be detected.

The method for detecting the BRAF fusion gene or the PXN or GMDS fusion gene according to the present invention comprises the step of amplifying a particular polynucleotide in a sample obtained from a subject through gene amplification reaction and preferably further comprises the step of detecting whether or not an amplified fragment having the size of interest is obtained.

PCR is suitable for quantitatively detecting the BRAF fusion gene or the PXN or GMDS fusion gene.

Thus, as described in the preceding section <Aspect (1-b) of detecting BRAF fusion gene>, the BRAF fusion gene can be detected by specifically detecting the respective expression levels of the 5'-terminal region and the 3'-terminal region of the BRAF gene and determining the ratio between the expression levels. Alternatively, the BRAF fusion gene can be detected by specifically detecting the respective expression levels of the 5'-terminal region and the 3'-terminal region of the partner gene, different from the BRAF gene, constituting the BRAF fusion gene together with the BRAF gene, and determining the ratio between the expression levels.

Also, as described in the preceding section <Aspect (1-b) of detecting PXN or GMDS fusion gene>, PCR can be suitably used in a method for detecting the PXN or GMDS fusion gene, comprising specifically detecting the respective expression levels of the 5'-terminal region and the 3'-terminal region of the PXN or GMDS gene and determining the ratio between the expression levels. Alternatively, the PXN or GMDS fusion gene can be detected by specifically detecting the respective expression levels of the 5'-terminal region and the 3'-terminal region of the partner gene, different from the PXN or GMDS gene, constituting the PXN or GMDS fusion gene together with the PXN or GMDS gene, and determining the ratio between the expression levels.

PCR and a primer design method for use therein can be performed by those skilled in the art according to a method known in the art.

For example, sense and antisense primers designed to be capable of specifically amplifying the 5'-terminal region of the BRAF gene, and sense and antisense primers designed to be capable of specifically amplifying the 3'-terminal region of the BRAF gene can be used.

For example, sense and antisense primers designed to be capable of specifically amplifying the 5'-terminal region of the PXN or GMDS gene, and sense and antisense primers designed to be capable of specifically amplifying the 3'-terminal region of the PXN or GMDS gene can be used.

==Real-Time PCR==

In the detection of the BRAF fusion gene or the PXN or GMDS fusion gene, the more quantitative analysis of PCR can be achieved by further using PCR amplification monitoring (real-time PCR) (Genome Res., 6 (10), 986, 1996) in the process of gene amplification. For example, ABI PRISM 7900 (PE Biosystems Japan Ltd.) can be used as the PCR amplification monitoring. The real-time PCR is a method known in the art, and an apparatus and a kit therefor are commercially available. The real-time PCR is conveniently performed using these commercially available products.

More specifically, when the BRAF fusion gene is, for example, a PXN- or GMDS-BRAF fusion gene and is detected by using its mRNA as an index, the sense primer (5'-primer or forward primer) is designed from an arbitrary site derived from the PXN or GMDS gene, and the antisense primer (3'-primer or reverse primer) is designed from an arbitrary site derived from the BRAF gene.

When the PXN or GMDS fusion gene is, for example, a PXN- or GMDS-BRAF fusion gene and is detected by using its mRNA as an index, the sense primer (5'-primer or forward primer) is designed from an arbitrary site derived from the PXN or GMDS gene, and the antisense primer (3'-primer or reverse primer) is designed from an arbitrary site derived from the BRAF gene.

==Multiplex PCR==

Multiplex PCR which detects all fusion polynucleotides using one reaction solution by mixing sense primers, as described above, corresponding to each partner gene that constitutes the BRAF fusion gene by its fusion with the BRAF gene and a plurality of fusion points can also be designed as PCR for detecting the BRAF fusion gene.

Multiplex PCR which detects all fusion polynucleotides using one reaction solution by mixing sense primers, as described above, corresponding to each partner gene that constitutes the PXN or GMDS fusion gene by its fusion with the PXN or GMDS gene and a plurality of fusion points can also be designed as PCR for detecting the PXN or GMDS fusion gene.

==Detection by Mass Spectrometry==

In the detection method using the gene amplification reaction method described above, mass spectrometry described in Japanese Patent Laid-Open No. 2012-100628 can be used for the analysis of the amplified fragment.

==Primer Set for Use in Detection==

The primer set for use in the detection method of the present invention for detecting the BRAF fusion gene is not particularly limited as long as the primer set can specifically amplify at least a portion of the BRAF fusion gene to be detected and permits detection of the BRAF fusion gene. Those skilled in the art can design the primer set on the basis of the nucleotide sequence of the polynucleotide to be detected.

The primer set for use in the detection method of the present invention for detecting the PXN or GMDS fusion gene is not particularly limited as long as the primer set can specifically amplify at least a portion of the PXN or GMDS fusion gene to be detected and permits detection of the PXN or GMDS fusion gene. Those skilled in the art can design the primer set on the basis of the nucleotide sequence of the polynucleotide to be detected.

The primers for the PCR amplification monitoring can be designed using primer design software (e.g., Primer Express; PE Biosystems Japan Ltd.) or the like. Since increase in the size of a PCR product deteriorates amplification efficiency, the sense primer and the antisense primer are appropriately set such that the size of an amplification product is 1 kb or smaller when mRNA or cDNA is to be amplified.

<Detection by Hybridization>

The mRNA can be detected by hybridization using a probe which hybridizes at least a partial polynucleotide of the BRAF fusion gene or the PXN or GMDS fusion gene to be detected.

Examples of the detection using the hybridization technique include Northern hybridization, dot blot, DNA microarray, and RNA protection.

==Probe (for mRNA)==

The probe for use in hybridization is preferably a probe which hybridizes under stringent conditions (preferably under more stringent conditions) to at least a portion of the BRAF fusion gene or the PXN or GMDS fusion gene or a complementary strand thereof.

<Detection of fusion protein>

Any technique well known to those skilled in the art for use in protein analysis, or any applied technique based on these techniques may be used as a technique of detecting the BRAF fusion protein or the PXN or GMDS fusion protein in a sample obtained from a subject.

Examples of the method for use in the detection of the BRAF fusion protein can include immunoassay, enzyme-linked immunosorbent assay (ELISA), two-antibody sandwich ELISA, fluorescent immunoassay, radioimmunoassay, Western blotting, immunohistochemistry, immunoprecipitation, iAEP (intercalated antibody-enhanced polymer), and FRET using an antibody specifically recognizing the BRAF protein or the partner protein, different from the BRAF protein, constituting the BRAF fusion protein together with the BRAF protein, or an antibody specifically recognizing the BRAF fusion protein. Alternatively, mass spectrometry or amino acid sequencing can be used alone or in combination with any of these methods.

Examples of the method for use in the detection of the PXN or GMDS fusion protein can include immunoassay, enzyme-linked immunosorbent assay (ELISA), two-antibody sandwich ELISA, fluorescent immunoassay, radioimmunoassay, Western blotting, immunohistochemistry, immunoprecipitation, iAEP (intercalated antibody-enhanced polymer), and FRET using an antibody specifically recognizing the PXN or GMDS protein or the partner protein, different from the PXN or GMDS protein, constituting the PXN or GMDS fusion protein together with the PXN or GMDS protein, or an antibody specifically recognizing the PXN or GMDS fusion protein. Alternatively, mass spectrometry or amino acid sequencing can be used alone or in combination with any of these methods.

Hereinafter, typical methods for detecting the protein will be illustrated, but are not limited to those described below.

[Typical Approach for Use in Detection]

The detection method using an antibody can conform to a method known in the art as described above. For example, the following methods can be used.

<Immunohistochemistry>

When the BRAF fusion protein or the PXN or GMDS fusion protein to be detected is, for example, a PXN- or GMDS-BRAF fusion protein, a tissue section likely to contain the fusion protein to be detected is immunostained with an anti-BRAF antibody binding to a polypeptide having the C-terminal region of the BRAF protein and an anti-PXN or anti-GMDS antibody binding to a polypeptide having the N-terminal region of the PXN or GMDS protein. The presence of the fusion protein to be detected can also be detected by using these antibodies located in proximity as an index. Alternatively, the tissue section is immunostained with an antibody specifically binding to a polypeptide having the N-terminal region of the BRAF protein and an antibody specifically binding to a polypeptide having the C-terminal region of the BRAF protein. The presence of the fusion protein to be detected can also be detected by using these antibodies localized distant from each other as an index. Alternatively, the tissue section is immunostained with an antibody specifically binding to a polypeptide having the N-terminal region of the PXN or GMDS protein and an antibody specifically binding to a polypeptide having the C-terminal region of the PXN or GMDS protein. The presence of the fusion protein to be detected can also be detected by using these antibodies localized distant from each other as an index.

Alternatively, the presence of the fusion protein to be detected may be detected by immunostaining using an antibody specifically binding to a polypeptide containing the fusion point.

<Western Blotting>

When the BRAF fusion protein or the PXN or GMDS fusion protein to be detected is, for example, a PXN- or GMDS-BRAF fusion protein, a cell extract likely to contain the fusion protein to be detected is electrophoresed by a method well known to those skilled in the art, and proteins thus isolated from the cell extract are blotted onto a membrane.

Then, the protein-blotted membrane is immunostained with an anti-BRAF antibody binding to a polypeptide having the N-terminal region of the BRAF protein and an anti-PXN or anti-GMDS antibody binding to the C-terminal region of the PXN or GMDS protein. The presence of the fusion protein to be detected can also be detected by using, as an index, the binding of the anti-BRAF antibody and the anti-PXN or anti-GMDS antibody to the desired positions on the membrane.

Alternatively, the presence of the fusion protein to be detected can also be detected by using an antibody specifically binding to a polypeptide containing the fusion point, and using, as an index, the binding of the antibody to the desired position on the membrane.

Alternatively, the presence of the fusion protein to be detected can also be detected by using an anti-BRAF antibody and using, as an index, the binding of the antibody to the PXN- or GMDS-BRAF fusion protein on the membrane. In this respect, the presence of the fusion protein to be detected may be detected by using, as an index, the binding of the anti-BRAF antibody to a position different from the predicted position of the wild-type BRAF protein on the membrane.

The PXN- or GMDS-BRAF fusion protein may be detected using the anti-PXN or anti-GMDS antibody on the same principle as in use of the anti-BRAF antibody.

<Immunoprecipitation>

When the BRAF fusion protein or the PXN or GMDS fusion protein to be detected is, for example, a PXN- or GMDS-BRAF fusion protein, a cell extract likely to contain the fusion protein to be detected is subjected to immunoprecipitation using any one of an anti-BRAF antibody binding to a polypeptide having the C-terminal region of the BRAF protein and an anti-PXN or anti-GMDS antibody binding to a polypeptide having the N-terminal region of the PXN or GMDS protein. The presence of the fusion protein to be detected can also be detected by detection using the other antibody in the precipitate. As described above, it is preferred to further use the detection antibody after the immunoprecipitation and the detection to confirm that the detected polypeptide has the size of the polypeptide of interest to be detected.

Alternatively, a cell extract likely to contain the BRAF fusion protein to be detected is subjected to immunoprecipitation using an anti-BRAF antibody binding to a polypeptide having the C-terminal region of the BRAF protein. The presence of the fusion protein to be detected can also be detected by further subjecting the precipitate to mass spectrometry and thereby confirming the presence of a protein that binds to the anti-BRAF antibody and differs in mass from wild-type BRAF.

A cell extract likely to contain the PXN or GMDS fusion protein to be detected is subjected to immunoprecipitation using an anti-PXN or anti-GMDS antibody binding to a polypeptide having the N-terminal region of the PXN or GMDS protein. The presence of the fusion protein to be detected can also be detected by further subjecting the precipitate to mass spectrometry and thereby confirming the presence of a protein that binds to the anti-PXN or anti-GMDS antibody and differs in mass from wild-type PXN or GMDS.

[Antibody for Use in Detection]

The antibody for use in the detection method according to the present invention is not particularly limited as long as the antibody specifically binds to the desired site in the BRAF fusion protein or the PXN or GMDS fusion protein. The antibody may be a monoclonal antibody or may be a polyclonal antibody. A monoclonal antibody and a polyclonal antibody may be used in combination. The antibody may be an immunoglobulin itself or may be an antibody fragment, for example, Fab, Fab', F(ab')$_2$, or Fv, which retains the ability to bind to an antigen. Any labeling or signal amplification method well known to those skilled in the art may be used for the detection of antibody binding.

<Labeling Approach>

In the gene (genomic DNA, mRNA, cDNA, etc.) and protein detection methods described above, probes, primers, amplification products, antibodies, etc. can be labeled by use of a technique known in the art. Examples thereof can include fluorescent labeling, chemiluminescent labeling, radiolabeling, enzymatic labeling, biotinylation, and avidin labeling.

In the detection method using a probe, the labeling method for labeling the probe can conform to a method known in the art as described above. For example, in the case of preparing a labeled nucleic acid probe from a BAC clone, an approach known in the art such as nick translation or random priming can be used. In this respect, the probe can be biotinylated with biotin-dUTP (e.g., manufactured by Roche Applied Science) and further labeled by treatment with a phosphor, a radioisotope, an enzyme, or the like bound with avidin.

In the detection method using an antibody, the labeling method for labeling the antibody can conform to a method known in the art as described above. Examples thereof include the following labeling methods.

[iAEP (Intercalated Antibody-Enhanced Polymer)]

Staining sensitivity can be enhanced by incorporating an intercalating antibody between a first antibody binding to the protein to be detected and a polymer reagent (Takeuchi et al., Clin Cancer Res, 2009 May 1; 15 (9): 3143-3149).

[Fluorescence Resonance Energy Transfer (FRET)]

For example, a probe based on the FRET phenomenon (FRET probe) can be used as an approach of detecting the proximity of two antibodies. One of the antibodies may be labeled with a donor fluorescent material (CFP, etc.), and the other antibody may be labeled with an acceptor fluorescent material (YFP, etc.). In this case, YFP becomes in an excided state by the FRET phenomenon when these fluorescent materials are positioned sufficiently close to each other. YEP restores its ground state by emitting fluorescence. The two antibodies located in proximity can be detected by detecting this fluorescence.

Determination of Applicable Subject to Treatment with BRAF-Inhibiting Substance

When the BRAF fusion gene to be detected or the BRAF fusion protein to be detected by the detection method of the present invention is detected from a sample obtained from a subject, the subject is a subject (patient) having a BRAF fusion-positive cancer and is an applicable subject to treatment with a BRAF-inhibiting substance.

Determination of Applicable Subject to Treatment with PXN- or GMDS-Inhibiting Substance When the PXN or GMDS fusion gene to be detected or the PXN or GMDS fusion protein to be detected by the detection method of the present invention is detected from a sample obtained from a subject, the subject is a subject (patient) having a PXN or GMDS fusion-positive cancer and is an applicable subject to treatment with a PXN- or GMDS-inhibiting substance.

Kit for Detection

The kit for detection of the present invention includes a kit for the detection of the BRAF fusion gene to be detected, or a kit for the detection of the BRAF fusion protein to be detected.

The kit for detection of the present invention includes a kit for the detection of the PXN or GMDS fusion gene to be detected, or a kit for the detection of the PXN or GMDS fusion protein to be detected.

The kit for the detection of the BRAF fusion gene to be detected or the kit for the detection of the PXN or GMDS fusion gene to be detected according to the present invention comprises probes that can be used in FISH fusion assay or FISH split assay in the detection method of the present invention, or sense and antisense primers designed to be capable of specifically amplifying at least a portion of the BRAF fusion gene or the PXN or GMDS fusion gene to be detected in the detection method of the present invention. The set of sense and antisense primers is a set of polynucleotides that function as primers for the amplification of a polynucleotide which is at least a partial polynucleotide of the BRAF fusion gene or the PXN or GMDS fusion gene and is to be amplified.

The kit for the detection of the BRAF fusion protein or the PXN or GMDS fusion protein to be detected according to the present invention comprises an antibody that can be used in the detection method of the present invention.

<Probe>

The kit for the detection of the BRAF fusion gene of the present invention can comprise one type or two or more types in combination of probe(s) which hybridizes under stringent conditions to at least a partial polynucleotide of the BRAF fusion gene or a complementary strand thereof and permits detection of the BRAF fusion gene.

The kit for the detection of the PXN or GMDS fusion gene of the present invention can comprise one type or two or more types in combination of probe(s) which hybridizes under stringent conditions to at least a partial polynucleotide of the PXN or GMDS fusion gene or a complementary strand thereof and permits detection of the PXN or GMDS fusion gene.

Examples of the probe can include any one or more types of probes described in the preceding section Technique for Use in Detection Method When the BRAF fusion gene or the PXN or GMDS fusion gene is, for example, a PXN- or GMDS-BRAF fusion gene, the kit may comprise only one or more types (preferably two or more types) of probes which hybridize to the polynucleotide derived from the BRAF gene, or only one or more types (preferably two or more types) of probes which hybridize to the polynucleotide derived from the PXN or GMDS gene, may comprise both of one or more types of probes which hybridize to the polynucleotide derived from the BRAF gene, and one or more types of probes which hybridize to the polynucleotide derived from the PXN or GMDS gene, or may comprise one or more types of probes which hybridize to a polynucleotide containing the fusion point of the BRAF fusion gene, or one or more types of probes which hybridize to a polynucleotide containing the fusion point of the PXN or GMDS fusion gene.

<Primer Set>

The kit for the detection of the BRAF fusion gene of the present invention can comprise one primer set or two or more primer sets in combination that can specifically amplify at least a portion of the BRAF fusion gene and permits detection of the BRAF fusion gene.

The kit for the detection of the PXN or GMDS fusion gene of the present invention can comprise one primer set or two or more primer sets in combination that can specifically amplify at least a portion of the PXN or GMDS fusion gene and permits detection of the PXN or GMDS fusion gene.

Examples of the primer set can include any one or more types of primer sets described in the preceding section <<Aspect of detection method of present invention>> or <<Technique for use in detection method>>.

The primer set of the present invention preferably includes
(1) a primer set for detecting a fusion gene of BRAF gene with PXN or GMDS gene, comprising an antisense primer designed from a polynucleotide moiety encoding the BRAF protein and a sense primer designed from a polynucleotide moiety encoding the PXN or GMDS protein, wherein the antisense primer consists of a nucleic acid molecule (preferably a nucleic acid molecule of at least 16 bases) which anneals under stringent conditions (preferably under more stringent conditions) to the "polynucleotide to be detected", and the sense primer consists of a nucleic acid molecule (preferably a nucleic acid molecule of at least 16 bases) which anneals under stringent conditions (preferably under more stringent conditions) to a complementary strand of the "polynucleotide to be detected".

In a more specific aspect of the primer set (1), the primer set of the present invention includes the following primer sets (2) to (5):
(2) a primer set of a sense primer consisting of an oligonucleotide of at least 16 consecutive nucleotides arbitrarily selected from nucleotide positions 1 to 962 of SEQ ID NO: 1 (PXNex6-BRAFex11), and an antisense primer consisting of an oligonucleotide complementary to an oligonucleotide of at least 16 consecutive nucleotides arbitrarily selected from nucleotide positions 963 to 2067 of SEQ ID NO: 1;
(3) a primer set of a sense primer consisting of an oligonucleotide of at least 16 consecutive nucleotides arbitrarily selected from nucleotide positions 1 to 372 of SEQ ID NO: 3 (GMDSex1-BRAFex9), and an antisense primer consisting of an oligonucleotide complementary to an oligonucleotide of at least 16 consecutive nucleotides arbitrarily selected from nucleotide positions 373 to 1651 of SEQ ID NO: 3;
(4) the following primer set for detecting the BRAF fusion gene shown in SEQ ID NO: 1:

```
PXN-441F:
                                    (SEQ ID NO: 8)
CCTGCTGCTGGAACTGAAC

BRAF-1444R:
                                    (SEQ ID NO: 9)
CTGCCACATCACCATGCCACT
``` and
(5) the following primer set for detecting the BRAF fusion gene shown in SEQ ID NO: 3:

```
GMDS-1F:
                                    (SEQ ID NO: 10)
GACATGGCACACGCACCG

BRAF-1444R:
                                    (SEQ ID NO: 9)
CTGCCACATCACCATGCCACT
```

As described in the preceding section ==PCR== in <Detection by gene amplification reaction method>, the primer set of the present invention may be a primer set for detecting the expression levels of the 5'-terminal region and the 3'-terminal region of the BRAF gene, or a primer set for detecting the expression levels of the 5'-terminal region and the 3'-terminal region of the partner gene that constitutes the fusion gene together with the BRAF gene.

In these primer sets (1) to (5), the interval between the positions at which the sense primer and the antisense primer are selected is preferably 1 kb or smaller, or the size of an amplification product obtained by amplification using the sense primer and the antisense primer is preferably 1 kb or smaller.

The primer of the present invention has a chain length of usually 15 to 40 bases, preferably 16 to 24 bases, more preferably 18 to 24 bases, particularly preferably 20 to 24 bases.

The primer set of the present invention can be used for amplifying and detecting the polynucleotide to be detected in the detection method of the present invention. Each primer contained in the primer set of the present invention can be produced by, for example, a chemical synthesis method, though the production method is not particularly limited thereto.

<Antibody>

The kit for the detection of the BRAF fusion protein of the present invention can comprise one type of antibody or two or more types of antibodies in combination specifically binding to an arbitrary site in the BRAF fusion protein. Specific examples thereof can include the antibodies described in the preceding section <Detection of fusion protein>.

The kit for the detection of the PXN or GMDS fusion protein of the present invention can comprise one type of antibody or two or more types of antibodies in combination specifically binding to an arbitrary site in the PXN or GMDS fusion protein. Specific examples thereof can include the antibodies described in the preceding section <Detection of fusion protein>.

When the BRAF fusion protein or the PXN or GMDS fusion protein is, for example, a PXN- or GMDS-BRAF fusion protein, the kit may comprise only one or more types (preferably two or more types) of antibodies binding to the polypeptide derived from the BRAF protein, or only one or more types (preferably two or more types) of antibodies binding to the polypeptide derived from the PXN or GMDS protein, may comprise both of one or more types of antibodies binding to the polypeptide derived from the BRAF protein, and one or more types of antibodies binding to the polypeptide derived from the PXN or GMDS protein, or may comprise one or more types of antibodies binding to a polypeptide containing the fusion point of the BRAF fusion protein, or one or more types of antibodies binding to a polypeptide containing the fusion point of the PXN or GMDS fusion gene.

Inhibiting Substance Screening Method

<Step of Screening for Substance that Inhibits Polypeptide>

The inhibiting substance screening method of the present invention can screen for a substance that inhibits the polypeptide to be detected and comprises the steps of:
(1) contacting the polypeptide to be detected or a cell expressing the polypeptide with a test substance;
(2) analyzing whether or not to inhibit the polypeptide; and
(3) selecting the substance that inhibits the polypeptide.
In the present specification, the phrase "inhibition of the polypeptide" includes the inhibition of the activity of the polypeptide and the inhibition of the expression of the polypeptide. The "inhibition" means the inhibition of at least a portion.

<Inhibiting Substance Screening Step and Index Therefor>

The screening method of the present invention includes
 (A) a method using a purified or crude polypeptide and using the in vitro activity inhibition of the polypeptide as an index,
 (B) a method using a cell expressing the polypeptide and using the activity inhibition of the polypeptide as an index, and
 (C) a method using a cell expressing the polypeptide and using the expression inhibition of the polypeptide as an index.

[(A) Method Using Purified or Crude Polypeptide and Using Activity Inhibition as Index]

The method (A) includes a method comprising the steps of: adding a test substance to the polypeptide in vitro for contact; analyzing whether or not the test substance inhibits the activity of the polypeptide by comparison with a control (polypeptide not contacted with the test substance); and selecting a substance that has inhibited the activity of the polypeptide.

The polypeptide activity can be measured in vitro by use of a kinase activity measurement method known in the art. For example, the amount of ADP formed through kinase reaction may be used as an index, or the tyrosine phosphorylation level of the polypeptide may be used as an index. A commercially available kinase activity measurement kit can also be used.

[(B) Method Using Polypeptide-Expressing Cell and Using Activity Inhibition as Index]

The method (B) includes a method comprising the steps of: adding a test substance to a cell expressing the polypeptide for contact; analyzing whether or not the test substance inhibits the activity of the polypeptide by comparison with a control (cell not contacted with the test substance); and selecting a substance that has inhibited the activity of the polypeptide.

The polypeptide activity can be measured in the cell by use of a kinase activity measurement method known in the art. For example, the amount of ADP formed through kinase reaction may be used as an index, or the tyrosine phosphorylation level of the polypeptide may be used as an index. A commercially available kinase activity measurement kit can also be used.

[(C) Method Using Polypeptide-Expressing Cell and Using Expression Inhibition as Index]

The method (C) includes a method comprising the steps of: adding a test substance to a cell expressing the polypeptide for contact; analyzing whether or not the test substance inhibits the expression of the polypeptide by comparison with a control (cell not contacted with the test substance); and selecting a substance that has inhibited the expression of the polypeptide.

The expression of the polypeptide in the cell can be analyzed by measuring a protein or mRNA level. The protein level can be measured by use of, for example, ELISA or immunoblot. The mRNA level can be measured by use of, for example, RT-PCR or Northern blot.

In this context, the BRAF fusion gene is a gene having tumorigenicity. Thus, the polypeptide-inhibiting substance selected by the inhibiting substance screening method of the present invention is useful as an active substance or a candidate substance thereof in a pharmaceutical composition for the treatment of a BRAF fusion-positive cancer. The method of the present invention can further comprise, if desired, the step of confirming that the inhibiting substance has therapeutic activity against a BRAF fusion-positive cancer.

Also, the PXN or GMDS fusion gene is a gene having tumorigenicity. Thus, the polypeptide-inhibiting substance selected by the inhibiting substance screening method of the present invention is useful as a therapeutic drug or a candidate substance thereof for a PXN or GMDS fusion-positive cancer. The method of the present invention can further comprise, if desired, the step of confirming that the inhibiting substance has therapeutic activity against a PXN or GMDS fusion-positive cancer.

The confirmation step can be carried out using an evaluation system known in the art. Examples thereof can include in vitro evaluation systems using cultured cells and evaluation systems using cancer-bearing animal models obtained by the transplantation of tumor cells. For the cancer-bearing animal models, a cell line may be temporarily established by culture from tumor tissues surgically resected from a patient and then transplanted to a recipient, or the tumor tissues may be directly transplanted to a recipient. The cancer-bearing animal model obtained by the latter approach is known as a PDX (patient-derived xenograft) animal model and is preferred for the evaluation system because gene expression profiles from repeated passages of subcutaneous tumor tissues are more similar to those from primary tumor as compared with the cell line-transplanted animal model.

The polypeptide-expressing cell can also be obtained by transfecting the desired cells with the polynucleotide of the present invention according to a routine method (see e.g., Molecular Cloning: A Laboratory Manual 4th Edition (2012), Cold Spring Harbor Laboratory Press). Specifically, the polypeptide-expressing cell (transformed cell) can be obtained, for example, by inserting cDNA which is the BRAF fusion gene or the PXN or GMDS fusion gene of the present invention to a recombinant vector and further transfecting cells with this vector.

Pharmaceutical Composition for Treatment of Cancer, Containing Inhibiting Substance The pharmaceutical composition for the treatment of a BRAF fusion-positive cancer of the present invention comprises a substance that inhibits the BRAF fusion gene or a transcript thereof. The pharmaceutical composition contains, for example, an inhibiting substance (e.g., a low-molecular compound, a double-stranded nucleic acid (including siRNA), a protein (including an antibody or an antibody fragment), a peptide, and other compounds) obtained by the inhibiting substance screening method of the present invention as an active ingredient and can contain, if desired, a pharmaceutically acceptable carrier.

The pharmaceutical composition for the treatment of a PXN or GMDS fusion-positive cancer of the present invention comprises a substance that inhibits the PXN or GMDS fusion gene or a transcript thereof. The pharmaceutical composition contains, for example, an inhibiting substance (e.g., a low-molecular compound, a double-stranded nucleic acid (including siRNA), a protein (including an antibody or an antibody fragment), a peptide, and other compounds) obtained by the inhibiting substance screening method of the present invention as an active ingredient and can contain, if desired, a pharmaceutically acceptable carrier.

<Substance that Inhibits BRAF Fusion Gene or Transcript, or PXN or GMDS Fusion Gene or Transcript>

Examples of the substance that inhibits the BRAF fusion gene or a transcript thereof can include kinase inhibitors, for example, BRAF-inhibiting substances and substances inhibiting the partner gene that constitutes the fusion gene together with the BRAF gene, or a transcript thereof.

Examples of the substance that inhibits the PXN or GMDS fusion gene or a transcript thereof can include kinase inhibitors, for example, PXN- or GMDS-inhibiting substances and substances inhibiting the partner gene that constitutes the fusion gene together with the PXN or GMDS gene, or a transcript thereof.

[Low-Molecular Compound]

Among the inhibiting substances described above, specific examples of the low-molecular compound can include trametinib (Japan Tobacco Inc.), sorafenib (Bayer Healthcare Pharmaceuticals Inc.), dabrafenib (GlaxoSmithKline LLC.), vemurafenib (PLX-4032, Hoffmann-La Roche Inc.), regorafenib (Bayer Healthcare Pharmaceuticals Inc.), N-{2,4-difluoro-3-[(5-pyridin-3-yl-1H-pyrrolo[2,3-b]pyridin-3-yl)carbonyl]phenyl}ethanesulfonamide, N-{3-[(5-chloro-1H-pyrrolo[2,3-b]pyridin-3-yl)carbonyl]-2,4-difluorophenyl}propane-1-sulfonamide, (1E)-5-(1-piperidin-4-yl-3-pyridin-4-yl-1H-pyrazol-4-yl)-2,3-dihydro-1H-inden-1-one oxime, GDC-0879 ((E)-2,3-dihydro-5-[1-(2-hydroxyethyl)-3-(4-pyridinyl)-1H-pyrazol-4-yl]-1H-inden-1-one oxime), RAF-265 (1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine), AZ628 (3-(2-cyanopropan-2-yl)-N-(4-methyl-3-(3-methyl-4-oxo-3,4-dihydroquinazolin-6-ylamino)phenyl)benzamide), and their pharmaceutically acceptable salts.

[Double-Stranded Nucleic Acid]

The double-stranded nucleic acid consists of a double-stranded nucleic acid (RNA or DNA) moiety and, preferably, 3'-terminal overhangs of the sense and antisense strands and induces RNAi. RNAi is an evolutionarily conserved phenomenon and occurs via a double-stranded nucleic acid of 21 to 23 bases formed by RNase III endonuclease (Genes Dev. 15, 485-490, 2001). Each 3'-overhang is an arbitrary nucleic acid of 1 or 2 bases, preferably 2 bases. The number of bases (21 to 23 bases) described above is the number of bases in each strand (sense or antisense strand) including the overhang. The sense strand and the antisense strand may have the same number of bases or may have different numbers of bases and preferably have the same number of bases.

For example, U (uridine), A (adenosine), G (guanosine), or C (cytidine) can be used as a ribonucleic acid constituting the 3'-overhang of the double-stranded nucleic acid. For example, dT (deoxythymidine), dA (deoxyadenosine), dG (deoxyguanosine), or dC (deoxycytidine) can be used as a deoxyribonucleic acid constituting the 3'-overhang.

The double-stranded nucleic acid that can be used as an active ingredient in the pharmaceutical composition of the present invention is not particularly limited as long as the double-stranded nucleic acid has an inhibitory effect on the BRAF fusion gene or an inhibitory effect on the PXN or GMDS fusion gene. For example, the double-stranded moiety can be designed on the basis of the nucleotide sequence of a polynucleotide containing the fusion point, for example, a nucleotide sequence including positions 962 and 963 of SEQ ID NO: 1, or a nucleotide sequence including positions 372 and 373 of SEQ ID NO: 3. Alternatively, the double-stranded moiety can be designed on the basis of the nucleotide sequence of a polynucleotide encoding a kinase moiety. The double-stranded nucleic acid of the present invention can be produced by a routine method (e.g., J. Am. Chem. Soc., 120, 11820-11821, 1998; and Methods, 23, 206-217, 2001). Commission manufacturers of double-stranded nucleic acids (e.g., RNAi Inc.) are well known to those skilled in the art and can be used in the production of the double-stranded nucleic acid. Also, the double-stranded nucleic acid can be designed using a siRNA sequence design system (Commercial siDirect®; RNAi Inc.).

[Protein and Antibody]

The antibody that can be used as an active ingredient in the pharmaceutical composition of the present invention is not limited as long as the antibody inhibits a transcript of the BRAF fusion gene or a transcript of the PXN or GMDS fusion gene, preferably a transcript of the PXN- or GMDS-BRAF gene. Examples thereof include antibodies inhibiting the activity of the BRAF fusion protein or the PXN or GMDS fusion protein, preferably kinase activity.

Polypeptide, Polynucleotide, Vector, and Transformed Cell of Present Invention

<Polypeptide of Present Invention>

The PXN or GMDS fusion protein, preferably the PXN-BRAF fusion protein or the GMDS-BRAF fusion protein, to be detected according to the detection method of the present invention is a novel protein in itself.

The PXN-BRAF fusion protein which is the polypeptide of the present invention is preferably any of the following polypeptides (a) to (d):

(a) a polypeptide consisting of the amino acid sequence represented by SEQ ID NO: 2, (b) a polypeptide comprising the amino acid sequence represented by SEQ ID NO: 2, and having tumorigenicity, (c) a polypeptide comprising an amino acid sequence with 80% or higher identity to the amino acid sequence represented by SEQ ID NO: 2, and having tumorigenicity, and (d) a polypeptide comprising an amino acid sequence derived from the amino acid sequence represented by SEQ ID NO: 2 by the deletion, substitution, and/or insertion of one or several amino acids, and having tumorigenicity.

The GMDS-BRAF fusion protein which is the polypeptide of the present invention is preferably any of the following polypeptides (a) to (d):

(a) a polypeptide consisting of the amino acid sequence represented by SEQ ID NO: 4, (b) a polypeptide comprising the amino acid sequence represented by SEQ ID NO: 4, and having tumorigenicity, (c) a polypeptide comprising an amino acid sequence with 80% or higher identity to the amino acid sequence represented by SEQ ID NO: 4, and having tumorigenicity, and (d) a polypeptide comprising an amino acid sequence derived from the amino acid sequence represented by SEQ ID NO: 4 by the deletion, substitution, and/or insertion of one or several amino acids, and having tumorigenicity.

<Polynucleotide of Present Invention>

The PXN or GMDS fusion gene, preferably the PXN-BRAF fusion gene or the GMDS-BRAF fusion gene, to be detected according to the detection method of the present invention is a novel gene in itself.

The polynucleotide of the present invention is not particularly limited as long as the polynucleotide encodes the polypeptide (i.e., the PXN or GMDS fusion protein, preferably the PXN-BRAF fusion protein or the GMDS-BRAF fusion protein) of the present invention (i.e., the PXN or GMDS fusion gene, preferably the PXN-BRAF fusion gene or the GMDS-BRAF fusion gene). The "polynucleotide encoding the PXN-BRAF fusion protein" may be a polynucleotide consisting only of a coding region in the PXN-BRAF fusion gene, may be the full-length genomic DNA of the PXN-BRAF fusion gene, or may be mRNA or cDNA of the PXN-BRAF fusion gene. Also, the "polynucleotide encoding the GMDS-BRAF fusion protein" may be a polynucleotide consisting only of a coding region in the GMDS-BRAF fusion gene, may be the full-length genomic DNA of the GMDS-BRAF fusion gene, or may be mRNA or cDNA of the GMDS-BRAF fusion gene.

<Vector of Present Invention>

The vector of the present invention is not particularly limited as long as the vector comprises the polynucleotide of the present invention. The vector of the present invention can be prepared by integrating the polynucleotide into an appropriate vector that can transform eukaryotic or prokaryotic host cells. The vector can comprise a sequence(s) necessary for the expression of the polynucleotide, for example, a promoter and an enhancer and can further comprise a sequence necessary for the confirmation of transfection of a host, for example, a drug resistance gene.

<Transformed Cell of Present Invention>

The transformed cell of the present invention can be prepared by transforming appropriate host cells, for example, eukaryotic or prokaryotic host cells with the vector of the present invention. The transformed cell of the present invention can be used for producing the polypeptide of the present invention.

EXAMPLES

Hereinafter, the present invention will be specifically described with reference to Examples. However, these Examples are not intended to limit the scope of the present invention.

In embodiments and Examples, methods described in standard protocols such as J. Sambrook, E. F. Fritsch & T. Maniatis (Ed.), Molecular cloning, a laboratory manual (3rd edition), Cold Spring Harbor Press, Cold Spring Harbor, New York (2001); and F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., or methods modified or altered from these methods are used unless otherwise specified. In the case of using commercially available reagent kits or measurement apparatuses, protocols attached thereto are used unless otherwise specified.

[Example 1] Detection of BRAF Gene Abnormality in Clinical Samples by FISH

A method is known which involves labeling 5'-terminal and 3'-terminal regions of the gene of interest with different dyes and observing the translocation or inversion, etc. of the gene. This method, one type of FISH, is called split assay. In the split assay, the 5'-terminal and 3'-terminal regions of the gene of interest to be examined for its chromosomal translocation or inversion, etc. are respectively stained with probes labeled with different fluorescent dyes. For example, these terminal regions are labeled with two types of fluorescent probes, a Texas Red (red)-labeled probe and a FITC (green)-labeled probe. As a result, one yellow signal (derived from green and red signals present in proximity) is detected under normal conditions (where no fusion gene is formed), while distant green and red signals are detected in the presence of translocation or inversion, etc.

BRAF gene abnormality in clinical samples was detected by the FISH split assay. Colorectal cancer tissues that were surgically resected, fixed in 20% formalin, and embedded in paraffin were sliced into a thickness of 4 μm, and these slices were placed on glass slides to prepare pathological sections. FISH was conducted according to the method described in the literature (Takeuchi K, Choi Y L, Soda M, Inamura K, Togashi Y, Hatano S, Enomoto M, Takada S, Yamashita Y, Satoh Y, Okumura S, Nakagawa K, Ishikawa Y, Mano H. Multiplex reverse transcription-PCR screening for EML4-ALK fusion transcripts. Clin Cancer Res. 2008; 14: 6618-6624). The prepared unstained sections were treated with Histology FISH Accessory Kit (Dako/Agilent Technologies, Inc.), followed by hybridization using a red (Texas Red) fluorescence-labeled BAC (bacterial artificial chromosome) clone (clone No. RP11-159M20) covering the 5'-terminal region of the BRAF gene, and a green (FITC) fluorescence-labeled BAC clone (clone No. RP11-759K14 or CTD-2337E12) covering the 3'-terminal region of the BRAF gene. Subsequently, the sections were further stained with 4,6-diamino-2-phenylindole. A fluorescence microscope BX51 (Olympus Corp.) was used in fluorescent observation. Sections suggesting genome structure abnormality were found by observed distant green and red signals. The study on approximately 1500 pathological samples identified two cases (colon cancer patient) suggesting genome structure abnormality in the BRAF gene region.

[Example 2] Gene Identification of BRAF Fusion Polynucleotide in Clinical Samples RNA derived from each tissue that suggested BRAF genome structure abnormality by the FISH analysis was used as a template in capture sequencing using Sure Select Human Kinome RNA Kit (Agilent Technologies, Inc.) and Miseq (Illumina, Inc.) to examine a gene located upstream of the kinase region of BRAF gene. The results demonstrated that a portion of PXN gene or GMDS gene is fused upstream of the BRAF gene kinase region.

[Example 3] Gene Isolation from PXN-BRAF and GMDS-BRAF Fusion Polynucleotides in Clinical Samples cDNA derived from each colorectal cancer clinical sample in which BRAF genome structure abnormality was suggested and a partner of the fusion gene was identified by the FISH analysis was used as a template in PCR using DNA polymerase (PrimeStar HS DNA polymerase), and each amplification product was cloned into pT7Blue-2. A forward primer GMDS-5'UTR (SEQ ID NO: 5) and a reverse primer BRAF-3'UTR (SEQ ID NO: 6) were used in combination as a primer set for isolation of the PXN-BRAF fusion polynucleotide gene. Also, a forward primer GMDS-5'UTR (SEQ ID NO: 7) and a reverse primer BRAF-3'UTR (SEQ ID NO: 6) were used in combination as a primer set for isolation of the GMDS-BRAF fusion polynucleotide gene.

As a result of sequencing the obtained amplification products (1914 bp and 1440 bp), a polynucleotide consisting of nucleotide sequences from start codon ATG to exon 6 of the PXN gene and from exon 11 to stop codon at exon 18 of the BRAF gene (PXNex6-BRAFex11; SEQ ID NO: 1) was able to be obtained. Also, a polynucleotide consisting of nucleotide sequences from start codon ATG to exon 1 of the GMDS gene and from exon 9 to stop codon at exon 18 of the BRAF gene (GMDSex1-BRAFex9; SEQ ID NO: 3) was able to be obtained.

The amino acid sequence (SEQ ID NO: 2) encoded by PXNex6-BRAFex11 was confirmed to have an amino acid substitution at one position (S73G) by comparison with the registered amino acid sequence of PXN (Ensemble database, Protein ID: ENSP00000288602). For the amino acid substitution, the first amino acid (e.g., "S" in S73G) means the amino acid in the registered amino acid sequence; the amino acid position subsequent thereto (e.g., "73" in S73G) means the amino acid position in SEQ ID NO: 2; and the final amino acid (e.g., "G" in S73G) means the amino acid in the amino acid sequence represented by SEQ ID NO: 2. C at position 348, which results in the amino acid substitution, in the nucleotide sequence represented by SEQ ID NO: 1 has been reported as a single-nucleotide polymorphism (rs4767884).

TABLE 1

| #1 | Primer name |
|----|-------------|
| #2 | Sequence |
| #3 | SEQ ID NO: |

[Example 4] Detection of PXN-BRAF Fusion Gene and GMDS-BRAF Fusion Gene cDNA from each fusion gene was detected by RT-PCR, which directly amplified a fusion part-containing region using the primers shown in Table 1, to show the presence of cDNA of the fusion gene in cancer tissues. Specifically, for the PXN-BRAF fusion gene, the sample-derived RNA template was subjected to PCR using a forward primer PXN-441F (SEQ ID NO: 8) designed on the PXN gene and a reverse primer BRAF-1444R (SEQ ID NO: 9) designed on the BRAF gene. As a result of electrophoresing the amplification product, a band having a size (521 bp) predicted from the primer set positions was observed. For the GMDS-BRAF fusion gene, the sample-derived RNA template was subjected to PCR using a forward primer GMDS-1F (SEQ ID NO: 10) designed on the GMDS gene and a reverse primer BRAF-1444R (SEQ ID NO: 9) designed on the BRAF gene. As a result of electrophoresing the amplification product, a band having a size (396 bp) predicted from the primer set positions was observed. The fusion genes were found detectable using clinical samples by designing primers on their genes.

[Example 5] Detection of PXN-BRAF Fusion Gene and GMDS-BRAF Fusion Gene in Clinical Samples by FISH Fusion Assay In order to confirm the partners in the fusion genes were fused on the genome, detection was performed by FISH fusion assay.

In the FISH fusion assay, two gene regions of interest that come in proximity due to chromosomal translocation or inversion, etc. are respectively stained with probes labeled with different fluorescent dyes. For example, these gene regions are labeled with two types of fluorescent probes, a Texas Red (red)-labeled probe and a FITC (green)-labeled probe. As a result, their respective red and green signals (distant red and green signals) are detected under normal conditions (where no fusion gene is formed), while a yellow signal resulting from the overlap of the red and green signals is detected when the two gene regions are located in proximity in the presence of translocation or inversion, etc.

Specifically, for the PXN-BRAF fusion gene, a red (Texas Red) fluorescence-labeled BAC clone (clone No. CTD-2308L15 or CTD-3139J18) covering the 5'-terminal region of the PXN gene, and a green (FITC) fluorescence-labeled BAC clone (clone No. RP11-759K14 or CTD-2337E12) covering the 3'-terminal region of the BRAF gene were used in combination.

For the GMDS-BRAF fusion gene, a red (Texas Red) fluorescence-labeled BAC clone (clone No. RP1-33B19, RP1-80B9, or RP1-136B1) covering the 5'-terminal region of the GMDS gene, and a green (FITC) fluorescence-labeled BAC clone (clone No. RP11-759K14 or CTD-2337E12) covering the 3'-terminal region of the BRAF gene were used in combination.

A fluorescence microscope BX51 (Olympus Corp.) was used in fluorescent observation. As a result of conducting the fusion assay using the pathological sections found positive to the fusion genes in Example 4, a signal (yellow) from the 5'-terminal region of the PXN gene and the 3'-terminal region of the BRAF gene located in proximity, or a signal (yellow) from the 5'-terminal region of the GMDS gene and the 3'-terminal region of the BRAF gene located in proximity was observed, confirming that the fusion genes were formed by chromosomal translocation or inversion, etc.

This method was found usable as a method for detecting the presence of these fusion genes.

[Example 6] Study on Tumorigenicity of PXN-BRAF and GMDS-BRAF Fusion Polypeptides In this Example, the PXN-BRAF fusion gene of SEQ ID NO: 1 obtained from a colorectal cancer clinical sample in Example 3 was used as cDNA encoding the PXN-BRAF fusion polypeptide. Also, the GMDS-BRAF fusion gene of SEQ ID NO: 3 obtained from a colorectal cancer clinical sample in Example 3 was used as cDNA encoding the GMDS-BRAF fusion polypeptide. The tumorigenicity of each fusion polypeptide was studied. Each cDNA described above was inserted to an expression vector pLenti6 (Invitrogen® (Life Technologies Corp.)), and mouse fibroblast line NIH3T3 cells were transfected with the resulting pLenti6-PXN-BRAF or pLenti6-GMDS-BRAF and cultured for 7 days. As a result, transformed foci were observed, as shown in FIGS. 1 (PXN-BRAF) and 2 (GMDS-BRAF). Such a transformed focus was observed in neither NIH3T3 cells treated only with a transfection reagent (control) nor NIH3T3 cells transfected with LacZ (not shown). In short, the transformed focus was observed only when the cells were transfected with the PXN-BRAF or GMDS-BRAF fusion polypeptide expression vector.

Figure 3:
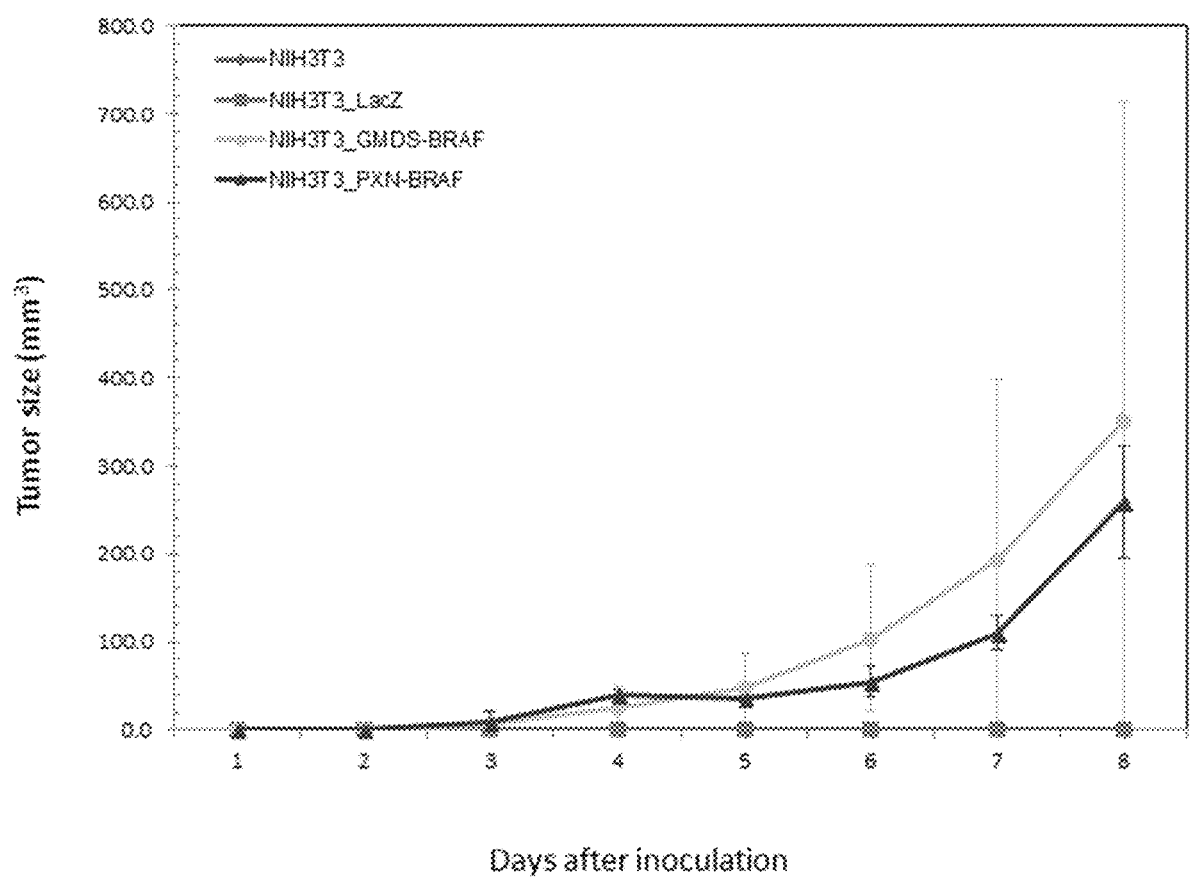
FIG. 3 is graph showing time-dependent change in tumor size from 1 to 8 days after inoculation in nude mice subcutaneously inoculated with the 3T3 fibroblasts transfected with the fusion gene PXN-BRAF or GMDS-BRAF.

The NIH3T3 cells transfected with the PXN-BRAF or GMDS-BRAF fusion polypeptide expression vector, the NIH3T3 cells treated only with a transfection reagent (control), and the NIH3T3 cells transfected with LacZ were subcutaneously inoculated at $1 \times 10^6$ cells each/body to nude mice. As a result, tumor formation was confirmed in the mouse inoculated with the NIH3T3 cells transfected with the fusion polypeptide expression vector. No tumor formation was confirmed in the mouse inoculated with the NIH3T3 cells treated only with a transfection reagent (control). The tumor sizes in both the mice on inoculation day 1 and later are shown in FIG. 3.

From these results, the PXN-BRAF or GMDS-BRAF fusion polypeptide had tumorigenicity, showing that the PXN-BRAF or GMDS-BRAF fusion polynucleotide is a causative gene of cancers.

As a result of transfecting NIH3T3 cells with cDNA encoding the full-length BRAF polypeptide, no transformed focus was observed, confirming that the full-length BRAF polypeptide is free from tumorigenicity.

[Example 7] Study on Sensitivity of PXN-BRAF or GMDS-BRAF Fusion Polypeptide-Expressing Cell to BRAF Inhibitor A mouse lymphoid cell line Ba/F3 is a cell line dependent on a growth factor IL-3 and requires IL-3 for its growth. The Ba/F3 cells are known to become able to grow without the addition of IL-3, when transfected with an oncogene (e.g., a tyrosine kinase fusion gene) (Daley G Q and Baltimore D. Proc Natl Acad Sci USA. 1988 December; 85 (23): 9312-9316).

In this Example, the sensitivity of parent line Ba/F3 cells and Ba/F3 cells transfected with pLenti6-PXN-BRAF or pLenti6-GMDS-BRAF prepared in Example 6 to a BRAF inhibitor (trametinib) was studied by adding a predetermined concentration of the BRAF inhibitor to 2000 cells and counting the number of cells after culture for 72 hours. For a more specific testing method, see, for example, the literature of Katayama et al. (Katayama R et al., Sci Transl Med, 2012 (4): 120ra17).

Figure 4:
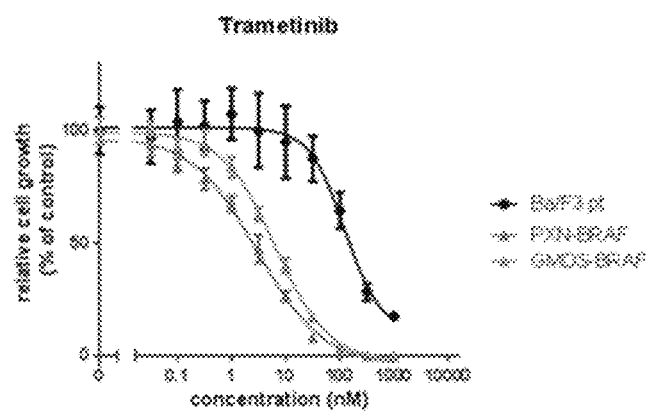
FIG. 4 is a graph showing the sensitivity of Ba/F3 cells expressing a PXN-BRAF or GMDS-BRAF fusion polypeptide to a BRAF inhibitor (trametinib).

The results are shown in FIG. 4. The BRAF inhibitor had no influence on the ability to grow of the parent line Ba/F3 cells (IL-3 concentration=0.5 ng/mL) as a control unless the concentration of the BRAF inhibitor exceeded an excessive level that exerted cytotoxicity. On the other hand, the cell growth of the Ba/F3 cells transfected with pLenti6-PXN-BRAF or pLenti6-GMDS-BRAF (without the addition of IL-3) was significantly inhibited by the BRAF inhibitor in a concentration-dependent manner as to both the fusion genes.

These results show that the BRAF inhibitor is effective for the treatment of PXN-BRAF or GMDS-BRAF fusion gene-positive cancer patients, and also shows that this evaluation system using the Ba/F3 cells transfected with pLenti6-PXN-BRAF or pLenti6-GMDS-BRAF can be used for screening for a drug effective for the treatment of such fusion gene-positive cancer patients.

[Example 8] Study on Phosphorylation Inhibition of PXN-BRAF or GMDS-BRAF Fusion Polypeptide by BRAF Inhibitor in PXN-BRAF or GMDS-BRAF Fusion Polypeptide-Expressing Cell In order to confirm that the growth inhibition of the PXN-BRAF or GMDS-BRAF fusion polypeptide-expressing cells by the BRAF inhibitor confirmed in Example 7 was attributed to the inhibition of the kinase activity of the PXN-BRAF or GMDS-BRAF fusion polypeptide against MEK (MAPK/ERK kinase), each cultured cell-derived extract treated with the BRAF inhibitor was subjected to Western blotting.

Figure 5:
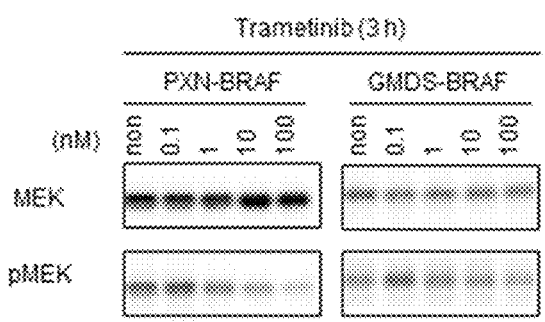
FIG. 5 is a photograph, instead of a drawing, showing results of treating Ba/F3 cells expressing a PXN-BRAF or GMDS-BRAF fusion polypeptide with a BRAF inhibitor and then carrying out the Western blotting of each cultured cell-derived extract.

The results are shown in FIG. 5. An anti-phosphorylated MEK antibody was used in the detection of phosphorylated MEK (pMEK in FIG. 5), and an anti-MEK antibody was used in the detection of MEK. The polypeptide level of MEK rarely differed between the presence and absence of the treatment with the BRAF inhibitor (and among the treatment concentrations). On the other hand, the MEK phosphorylation of the PXN-BRAF or GMDS-BRAF fusion polypeptide was significantly decreased by the treatment with the BRAF inhibitor in a concentration-dependent manner, confirming that the MEK phosphorylation of the PXN-BRAF or GMDS-BRAF fusion polypeptide is inhibited by the inhibition of the kinase activity of the PXN-BRAF or GMDS-BRAF fusion polypeptide.

Thus, the present invention demonstrated that a fusion gene of the PXN or GMDS gene with the BRAF gene is present in some digestive organ cancer patients, and the gene is responsible for their cancers. These results demonstrated that cancer patients to be treated with a BRAF inhibitor can be selected by detecting the PXN-BRAF or GMDS-BRAF fusion gene, preferably by detecting PXNex6-BRAFex11 or GMDSex1-BRAFex9.

INDUSTRIAL APPLICABILITY

The detection method of the present invention is useful in the determination of a BRAF fusion-positive cancer patient. The kit and the primer set for detection of the present invention can be used in the detection method. The inhibiting substance screening method of the present invention can be used for screening for a substance effective for the treatment of the fusion-positive cancer patient. The substance obtained by the screening can be used as an active ingredient in a pharmaceutical composition for the treatment of the fusion-positive cancer. The cancer in a patient determined as the fusion-positive cancer patient by the detection method can be treated by the administration of the substance.

The detection method of the present invention is useful in the determination of a PXN or GMDS fusion-positive cancer patient. The kit and the primer set for detection of the present invention can be used in the detection method. The inhibiting substance screening method of the present invention can be used for screening for a substance effective for the treatment of the fusion-positive cancer patient. The substance obtained by the screening can be used as an active ingredient in a pharmaceutical composition for the treatment of the fusion-positive cancer. The cancer in a patient determined as the fusion-positive cancer patient by the detection method can be treated by the administration of the substance.

The present invention is described above with reference to particular aspects. However, changes or modifications obvious to those skilled in the art are included in the scope of the present invention.

Free Text of Sequence Listing

The nucleotide sequences represented by SEQ ID NOs: 5 to 10 of the Sequence Listing are synthetic primer sequences.

The invention claimed is:

1. A kit for detecting a GMDS-BRAF fusion gene in a sample obtained from a subject, the kit comprising a sense primer and an antisense primer, the sense primer and antisense primer designed to be capable of specifically amplifying a polynucleotide encoding a polypeptide which is a fusion protein of a GMDS protein with a BRAF protein, wherein the sense primer consists of an oligonucleotide of at least 16 consecutive nucleotides arbitrarily selected from nucleotide positions 1 to 372 of SEQ ID NO: 3, and the antisense primer consists of an oligonucleotide complementary to an oligonucleotide of at least 16 consecutive nucleotides arbitrarily selected from nucleotide positions 373 to 1651 of SEQ ID NO: 3.

2. A method for detecting a GMDS-BRAF fusion gene encoding a fusion protein of a GMDS protein with a BRAF protein in a sample obtained from a subject, wherein the sample is DNA or mRNA, the method comprising detecting the GMDS-BRAF fusion gene using a kit for detecting the GMDS-BRAF fusion gene in the sample, the kit comprising a sense primer and an antisense primer, the sense primer and antisense primer designed to be capable of specifically amplifying a polynucleotide encoding a polypeptide which is the fusion protein, wherein the sense primer consists of an oligonucleotide of at least 16 consecutive nucleotides arbitrarily selected from nucleotide positions 1 to 372 of SEQ ID NO: 3, and the antisense primer consists of an oligonucleotide complementary to an oligonucleotide of at least 16 consecutive nucleotides arbitrarily selected from nucleotide positions 373 to 1651 of SEQ ID NO: 3.

* * * * *